US010667775B2

(12) United States Patent
Anderson et al.

(10) Patent No.: US 10,667,775 B2
(45) Date of Patent: *Jun. 2, 2020

(54) PERCUTANEOUS CORONARY INTERVENTION (PCI) PLANNING INTERFACE AND ASSOCIATED DEVICES, SYSTEMS, AND METHODS

(71) Applicant: VOLCANO CORPORATION, San Diego, CA (US)

(72) Inventors: David Anderson, Temecula, CA (US); Andrew Tochterman, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1225 days.

This patent is subject to a terminal disclaimer.

(21) Appl. No.: 14/939,172

(22) Filed: Nov. 12, 2015

(65) Prior Publication Data

US 2016/0135787 A1    May 19, 2016

Related U.S. Application Data

(60) Provisional application No. 62/080,023, filed on Nov. 14, 2014.

(51) Int. Cl.
*A61B 6/00* (2006.01)
*G06F 19/00* (2018.01)
(Continued)

(52) U.S. Cl.
CPC .......... *A61B 6/504* (2013.01); *A61B 5/02007* (2013.01); *A61B 5/02158* (2013.01);
(Continued)

(58) Field of Classification Search
None
See application file for complete search history.

(56) References Cited

U.S. PATENT DOCUMENTS 7,930,014 B2    4/2011   Huennekens et al.
8,548,778 B1    10/2013  Hart
(Continued)

FOREIGN PATENT DOCUMENTS

JP   2007075141 A   3/2007
WO   2006093776 A1  9/2006
(Continued)

*Primary Examiner* — Jason T Yen

(57) ABSTRACT

A method of evaluating a vessel of a patient is provided. The method includes outputting, to a display device, a screen display including: a visualization based on pressure measurements obtained from a first instrument and a second instrument positioned within the vessel of the patient while the second instrument is moved longitudinally through the vessel and the first instrument remains stationary within the vessel; and a visual representation of a vessel; receiving a user input to modify the visualization to simulate a therapeutic procedure; and updating the screen display, in response to the user input, including modifying the visualization based on the user input. A system for evaluating a vessel of a patient is also provided. The system includes first and second instruments sized and shaped for introduction into the vessel of the patient; and a processing system communicatively coupled to the first and second instruments and a display device.

20 Claims, 29 Drawing Sheets

(51) Int. Cl.
*A61B 5/00* (2006.01)
*A61B 5/0215* (2006.01)
*A61B 5/02* (2006.01)
*A61B 8/12* (2006.01)
*A61B 8/00* (2006.01)
*A61B 34/10* (2016.01)

(52) U.S. Cl.
CPC ............... *A61B 5/743* (2013.01); *A61B 8/12* (2013.01); *A61B 8/463* (2013.01); *A61B 8/468* (2013.01); *G06F 19/32* (2013.01); *A61B 5/4848* (2013.01); *A61B 5/7435* (2013.01); *A61B 5/7475* (2013.01); *A61B 2034/104* (2016.02)

(56) References Cited

U.S. PATENT DOCUMENTS

| | | |
|---|---|---|
| 9,339,348 B2 | 5/2016 | Davies et al. |
| 2005/0010138 A1 | 1/2005 | Mangiardi |
| 2007/0066888 A1* | 3/2007 | Maschke ................ A61B 18/24 600/424 |
| 2008/0221442 A1 | 9/2008 | Tolkowsky et al. |
| 2009/0177090 A1* | 7/2009 | Grunwald ............ A61B 5/7405 600/454 |
| 2010/0104167 A1* | 4/2010 | Sakaguchi ................ G06T 7/11 382/132 |
| 2014/0187920 A1 | 7/2014 | Millett et al. |
| 2015/0025330 A1* | 1/2015 | Davies ............... A61B 5/02154 600/301 |

FOREIGN PATENT DOCUMENTS

| | | |
|---|---|---|
| WO | WO 2010/058398 A2 | 5/2010 |
| WO | WO 2012/014212 A2 | 2/2012 |
| WO | WO 2012/093260 A1 | 7/2012 |
| WO | WO 2012/093266 A1 | 7/2012 |
| WO | 2012166332 A1 | 12/2012 |
| WO | WO 2013/028612 A2 | 2/2013 |

\* cited by examiner

PERCUTANEOUS CORONARY INTERVENTION (PCI) PLANNING INTERFACE AND ASSOCIATED DEVICES, SYSTEMS, AND METHODS

CROSS REFERENCE TO RELATED APPLICATIONS

The present application claims priority to and the benefit of the U.S. Provisional Patent Application No. 62/080,023, filed Nov. 14, 2014, which is hereby incorporated by reference in its entirety.

TECHNICAL FIELD

The present disclosure relates generally to the assessment of vessels for percutaneous coronary intervention (PCI) planning. For example, some embodiments of the present disclosure are suited for determining physiologic parameters for the PCI, such as stent position, stent length, stent diameter, etc., by visualizing and varying the properties of a graphical representation of a stent positioned within a vessel using a graphical user interface.

BACKGROUND

Innovations in diagnosing and verifying the level of success of treatment of disease have progressed from solely external imaging processes to include internal diagnostic processes. In addition to traditional external image techniques such as X-ray, MRI, CT scans, fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy.

One exemplary type of procedure involves pressure measurements within a blood vessel. A currently accepted technique for assessing the severity of a stenosis in the blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Another technique for assessing blood vessels utilizes Instant Wave-Free Ratio™ Functionality (iFR® Functionality) (both trademarks of Volcano Corp.), which includes the determination of a pressure ratio across a stenosis during the wave-free period, when resistance is naturally constant and minimized in the cardiac cycle. The iFR modality does not require administration of a hyperemic agent. The normal value of iFR in a healthy vessel is 1.00, while values less than about 0.89 are generally deemed significant and require treatment.

When an occluded blood vessel that requires treatment is identified, a percutaneous coronary intervention (PCI) is a therapeutic procedure that can be utilized to treat the vessel. A PCI includes angioplasty and positioning a stent across the stenosis to open the vessel. Clinicians conventionally rely on angiography and physiologic measurements of pressure and/or flow, which are not meaningfully connected, to plan a therapeutic intervention. Planning the therapeutic intervention can include selecting various parameters related to the stent, such as positioning, length, diameter, etc. Because it is difficult to integrate the various sources of data, there is difficulty in developing the therapeutic plan. Further, there is little ability to predict the efficacy of the therapeutic intervention based on the available data. For example, a clinician conventionally cannot determine, with a clinical certainty that is supported by the collected data, what the effect of changing the positioning and/or length of a stent is on the efficacy of the stent placement.

Accordingly, there remains a need for improved devices, systems, and methods for assessing the severity of a blockage in a vessel and, in particular, a stenosis in a blood vessel. There also remains a need for improved devices, systems, and methods for planning a PCI by connecting the angiography and physiologic data in a way that allows clinicians to efficiently plan and evaluate the proposed therapy. Further, there remains a need for providing visual depictions of a vessel and a proposed therapeutic intervention, such as a stent, in the vessel that allow a clinician to plan, evaluate, and change the proposed therapy in a manner supported by the collected physiologic data.

SUMMARY

Embodiments of the present disclosure are configured to provide a graphical user interface that illustrates a stent positioned within a blood vessel to allow a doctor to effectively plan a surgical procedure known as a percutaneous coronary intervention (PCI). The position and length of the stent within the blood vessel can be changed based on user input. The image of the blood vessel can include various annotations that assist the doctor, including pressure ratio(s) calculated along the vessel's length, locations along the vessel associated with pressure ratio(s), and the name of the vessel. In some embodiments, a menu of stents is provided to a doctor such that the doctor can select a stent that is in stock and available for use at the hospital while planning the surgical procedure.

In an exemplary embodiment, a method of evaluating a vessel of a patient are provided. The method includes outputting, to a display device, a screen display including: a visualization based on pressure measurements obtained from a first instrument and a second instrument positioned within the vessel of the patient while the second instrument is moved longitudinally through the vessel and the first instrument remains stationary within the vessel; and a visual representation of a vessel; receiving a user input to modify the visualization to simulate a therapeutic procedure; and updating the screen display, in response to the user input, including modifying the visualization based on the user input.

In some embodiments, the method further includes obtaining angiography data simultaneously as obtaining the pressure measurements, wherein the visual representation of the vessel includes an angiographic image of the vessel, and wherein the visualization includes a graphical overlay on the angiographic image. In some embodiments, obtaining the pressure measurements includes moving the second instrument at a constant or a non-constant speed through the vessel. In some embodiments, the visualization includes a graphical representation of a stent positioned in the visual representation of the vessel, and wherein the therapeutic procedure is a percutaneous coronary intervention. In some embodiments, the method further includes determining physiological parameters for a stent to be deployed in the vessel based on the characteristics of the graphical representation of the stent. In some embodiments, the physiological parameters include at least one of stent position, stent length, and stent diameter; and the characteristics of the graphical representation of the stent include at least one of position, length, and diameter.

In some embodiments, the method further includes automatically calculating at least one of the stent length and the length of the graphical representation of the stent based on at least one of the angiography data, the obtained pressure measurements, and a pressure ratio calculated based on the obtained pressure measurements, wherein the visualization includes a graphical representation of a stent having the calculated length. In some embodiments, the method further includes determining at least one of the stent length and the length of the graphical representation of the stent based on the user input, wherein the visualization includes a graphical representation of a stent having the determined length. In some embodiments, the method further includes determining at least one of the stent diameter and the diameter of the graphical representation of the stent based on at least one of the angiography data and intravascular imaging data obtained within the vessel. In some embodiments, receiving a user input includes receiving a user input to move the graphical representation of the stent within the visual representation of the vessel, and wherein modifying the visualization includes outputting the graphical representation of the stent at the position based on the user input. In some embodiments, receiving a user input includes receiving a user input to change the length of the graphical representation of the stent within the visual representation of the vessel, and wherein modifying the visualization includes outputting the graphical representation of the stent with the length based on the received user input.

In some embodiments, the method further includes outputting a plurality of graphical representations of stents. In some embodiments, the method further includes compiling the plurality of graphical representations of stents based on an inventory database of stents associated with a clinical environment. In some embodiments, the method further includes at least one of: receiving a user input to select one of the plurality of graphical representations of stents, wherein the visualization includes the selected graphical representation of a stent positioned in the visual representation of the vessel; and automatically selecting a graphical representation of a stent from among a plurality of graphical representations of stents based on at least one of the angiography data, the obtained pressure measurements, and a pressure ratio calculated based on the obtained pressure measurements, wherein the visualization includes the automatically selected graphical representation of a stent from among the plurality of graphical representations of stents.

In some embodiments, the method further includes calculating a pressure ratio within the vessel based on the obtained pressure measurements, and wherein the visualization further includes the calculated pressure ratio. In some embodiments, the visualization further includes at least one of: a marker indicative of a location within the vessel associated with the obtained pressure measurements; and the calculated pressure ratio positioned adjacent to the marker indicative of the location within the vessel. In some embodiments, the method further includes automatically identifying the vessel, and wherein the visualization further includes a label indicative of the determined identity of the vessel.

In another exemplary embodiment, a system for evaluating a vessel of a patient is provided. The system includes a first instrument sized and shaped for introduction into the vessel of the patient; a second instrument sized and shaped for introduction into the vessel of the patient; and a processing system communicatively coupled to the first and second instruments and a display device, the processing system configured to: receive pressure measurements from the first instrument and the second instrument positioned within the vessel of the patient while the second instrument is moved longitudinally through the vessel and the first instrument remains stationary within the vessel; output, to the display device, a screen display including: a visualization based on pressure measurements received from the first instrument and the second instrument; and a visual representation of a vessel; receive a user input to modify the visualization to simulate a therapeutic procedure; and update the screen display, in response to the user input, including modifying the visualization based on the user input.

In some embodiments, the visual representation of the vessel includes an angiographic image of the vessel, and wherein the visualization includes a graphical overlay on the angiographic image. In some embodiments, the visualization includes a graphical representation of a stent positioned in the visual representation of the vessel, and wherein the therapeutic procedure is a percutaneous coronary intervention. In some embodiments, the processing system is further configured to: determine physiological parameters for a stent to be deployed in the vessel based on the characteristics of the graphical representation of the stent. In some embodiments, the physiological parameters include at least one of stent position, stent length, and stent diameter; and the characteristics of the graphical representation of the stent include at least one of position, length, and diameter.

In some embodiments, the processing system is further configured to automatically calculate at least one of the stent length and the length of the graphical representation of the stent based on at least one of the angiography data, the received pressure measurements, and a pressure ratio calculated based on the received pressure measurements, wherein the visualization includes a graphical representation of a stent having the calculated length. In some embodiments, the processing system is further configured to determine at least one of the stent length and the length of the graphical representation of the stent based on the user input, wherein the visualization includes a graphical representation of a stent having the determined length.

In some embodiments, the processing system is further configured to automatically calculate at least one of the stent diameter and the diameter of the graphical representation of the stent based on at least one of angiography data and intravascular ultrasound (IVUS) data. In some embodiments, the processing system is configured receive a user input by receiving a user input to move the graphical representation of the stent within the visual representation of the vessel, and wherein the processing system is configured to modify the visualization by outputting the graphical representation of the stent at a location based on the user input. In some embodiments, the processing system is configured receive a user input by receiving a user input to change a length of the graphical representation of the stent within the vessel, and wherein the processing system is configured to modify the visualization by outputting the graphical representation of the stent with the length based on the received user input.

In some embodiments, the processing system is further configured to output a plurality of graphical representations of stents. In some embodiments, the processing system is further configured to compile the plurality of graphical representations of stents based on an inventory database of stents associated with a clinical environment. In some embodiments, the processing system is further configured to do at least one of: receive a user input to select one of the plurality of graphical representations of stents, wherein the visualization includes the selected graphical representation of a stent from among the plurality of graphical representations of stents; and automatically select a graphical representation of a stent from among a plurality of graphical representations of stents based on at least one of the angiography data, the received pressure measurements, and a pressure ratio calculated based on the received pressure measurements, wherein the visualization includes the automatically selected graphical representation of a stent from among the plurality of graphical representations of stents.

In some embodiments, the processing system is further configured to calculate a pressure ratio within the vessel based on the receive pressure measurements, and wherein the visualization further includes the calculated pressure ratio. In some embodiments, the visualization further includes at least one of: a marker indicative of a location within the vessel associated with the obtained pressure measurements; the calculated pressure ratio positioned adjacent to the marker indicative of the location within the vessel. In some embodiments successive markers are positioned along the visual representation of the vessel at unequally spaced intervals. In some embodiments, the processing system is further configured to automatically identify the vessel, and wherein the visualization further includes a label indicative of the determined identity of the vessel.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
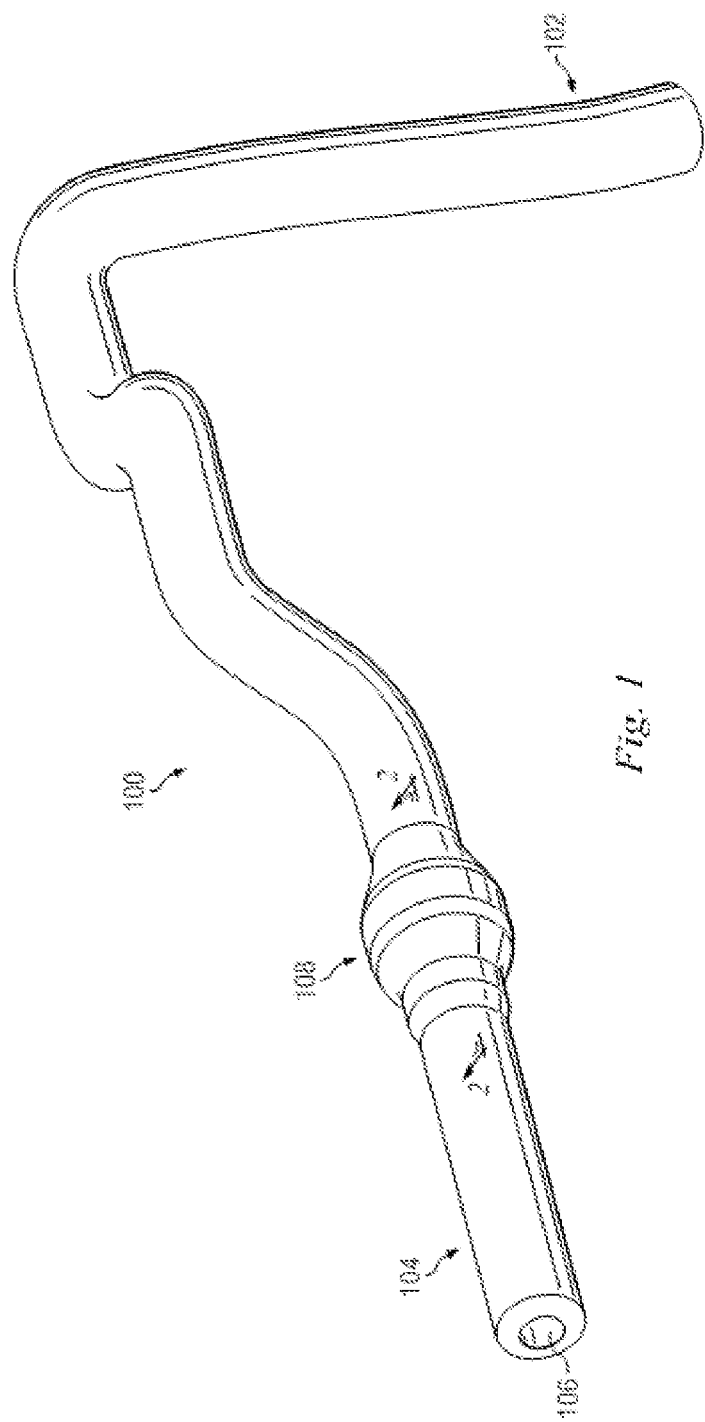
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
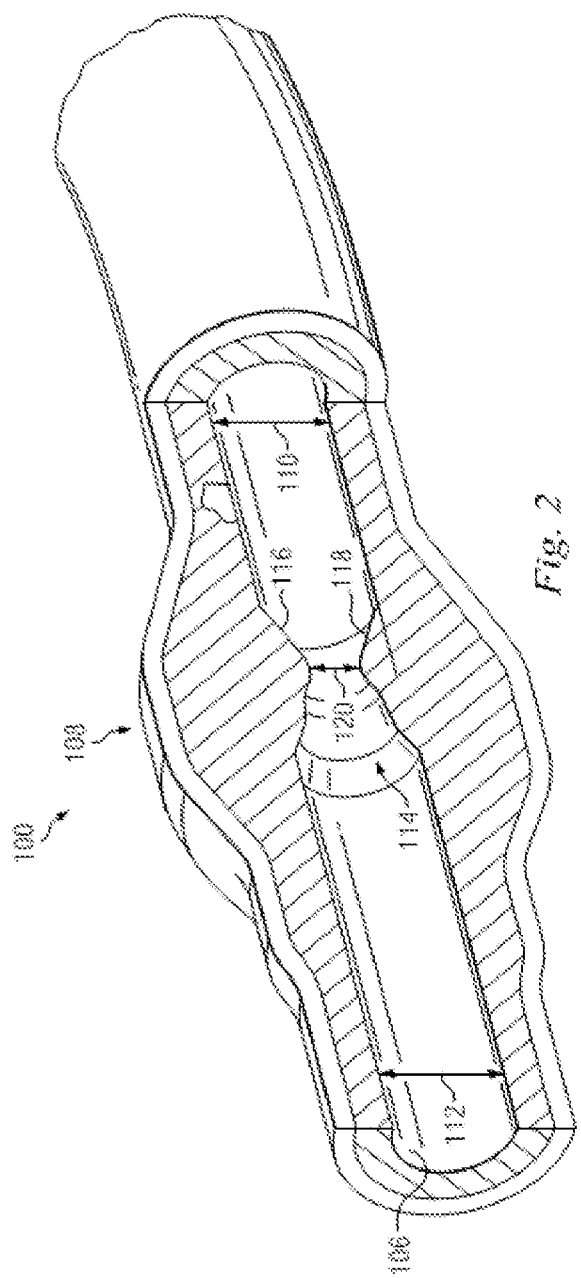
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
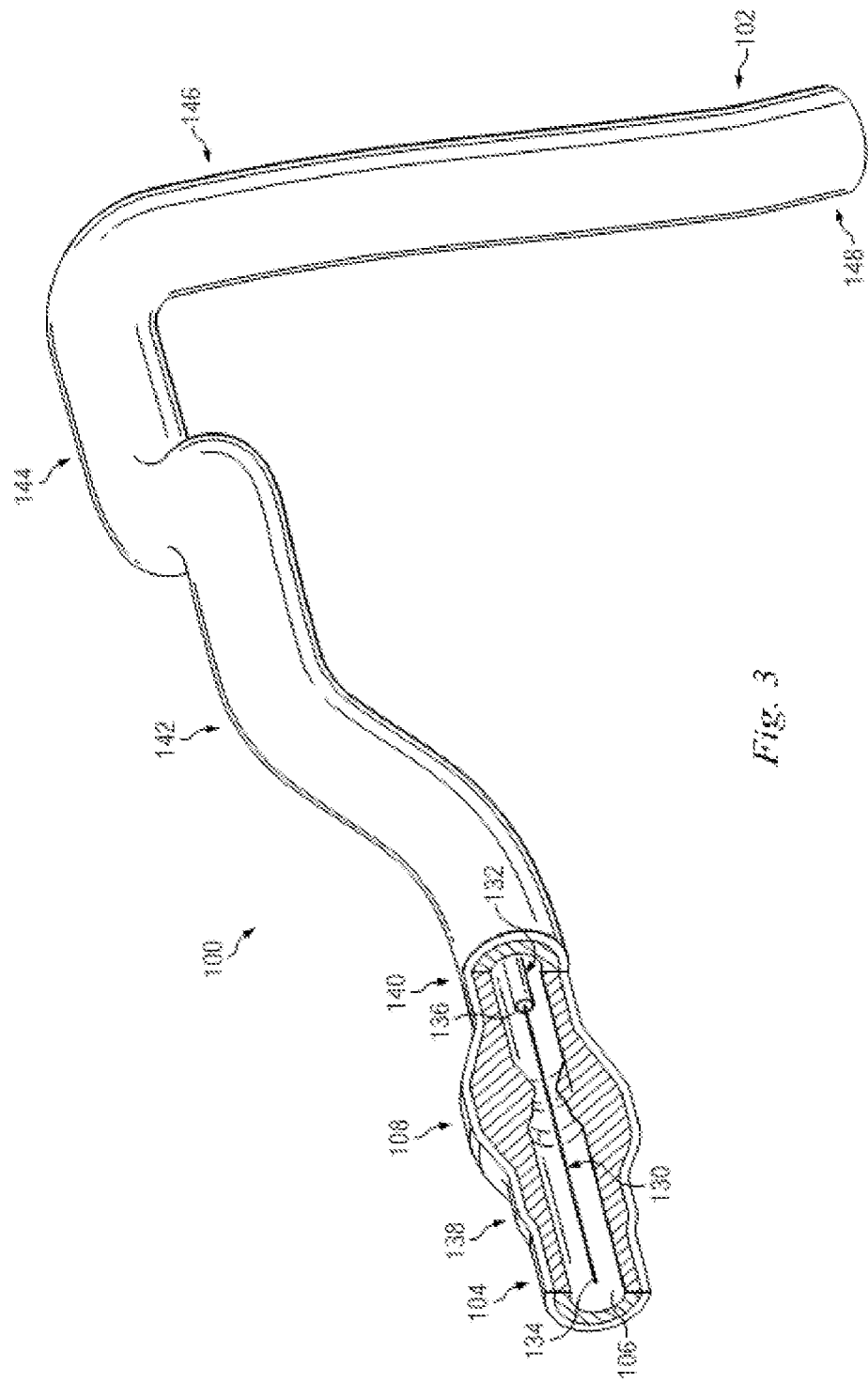
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity and/or volume), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the Verrata® pressure guide wire, the PrimeWire Prestige® PLUS pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less. In some embodiments, the instrument 130 has an outer diameter of 0.035" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity and/or volume), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

The instruments 130 and/or 132 can be used to conduct medical sensing procedures associated with Instant Wave-Free Ratio™ Functionality (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," hereby incorporated by reference in its entirety, which discloses the use of pressure ratios that are available without application of a hyperemic agent. Further, medical sensing procedures associated with compensated Pd/Pa ratios suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety, can be conducted using the instruments 130 and/or 132.

Figure 4:
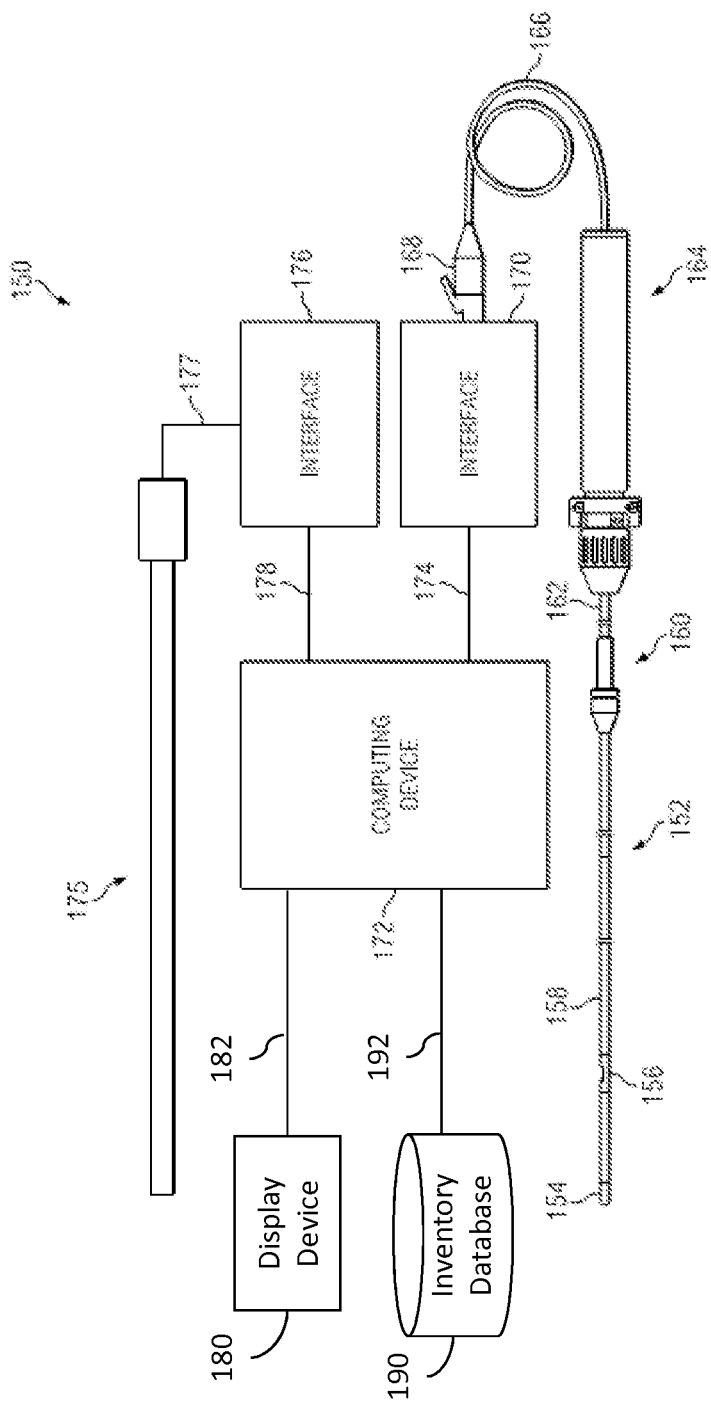
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i® Imaging System, each available from Volcano Corporation. In some instances, the computing device 172 is portable (e.g., handheld, on a rolling cart, etc.). In some instances, all or a portion of the computing device 172 can be implemented as a bedside controller such that one or more processing steps described herein can be performed by processing component(s) of the bedside controller. An exemplary bedside controller is described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

The computing device 172 is communicatively coupled to a display device 180 via a connection 182. In some embodiments, the display device 172 is a component of the computing device 172, while in other embodiments, the display device 172 is distinct from the computing device 172. In some embodiments, the display device 172 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The computing device 172 can generate screen displays including data collected by the instruments 152 and 175 and other instruments, quantities computed based on the collected data, visualizations of the vessel in which the data is collected, and visualizations based on the collected data and computed quantities. Exemplary screen displays are illustrated in FIGS. 7-28. The computing device 172 can provide the display data associated with the screen displays to the display device 180.

The computing device 172 can additionally be communicatively coupled to a user interface device. The user interface device permits a user to interact with the screen displays on the display device 180. For example, the user can provide a user input to modify all or a portion of the screen display using the user interface device. Exemplary user inputs and the corresponding modifications to the screen display are illustrated in FIGS. 7-28. In some embodiments, the user interface device is a separate component from the display device 180. In other embodiments, the user interface device is part of the display device 180. For example, the user interface device can be implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. In such embodiments, a user input can be a touch input received on the touch sensitive display of the bedside controller.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

In some embodiments, the system 150 can additionally include a bedside controller, such as the bedside controller described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The bedside controller may be utilized by a clinician to control instruments 152 and 175 to acquire pressure data during a procedure, watch real-time medical pressure measurements (e.g., visual representations of pressure data, such as pressure waveforms, numerical values, etc.), compute pressure ratio(s) based on the collected pressure data, and interact with the obtained medical sensing data, a visual representation of the obtained medical sensing data and/or computed pressure ratio(s), a visualization based on the obtained medical sensing data and/or computed pressure ratio(s), and/or a visual representation of the vessel 100. In that regard, the bedside controller can be communicatively coupled to the computing device 172, the interfaces 170 and 176, and/or the instruments 152 and 175.

In some embodiments, the system 150 can include an inventory database 190 associated with a clinical environment, such as a hospital or other healthcare facility at which a PCI would be carried out on a patient. The inventory database can store various data about stents that are available to a clinician for use. The data can include manufacturer names, length, diameter, material, quantity available at the hospital, quantity available for immediate use, resupply frequency, next shipment date, and other suitable information. As described with respect to FIGS. 27 and 28, the computing device 172 can compile a plurality of stent options based on the inventory database 190 and provide a selection menu to the clinician. The computing device 172 can provide automatically recommend a particular stent (e.g., a stent from a particular manufacturer, with a particular length, diameter, and/or material) based on the PCI planning conducted using the graphical user interface. The computing device 172 can also receive a user input selecting a particular stent and provide it into the graphical user interface such that a clinician can assess the efficacy of treatment using the selected stent. The computing device 172 is communicatively coupled to the inventory database 190 via a connection 192. The connection 192 can be representative of one or more network connections that communicatively couple the computing device 172 with a computing system of the healthcare facility.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include FFR (e.g., a pressure ratio value calculated as a first instrument is moved through a vessel relative to a second instrument, including across at least one stenosis of the vessel), Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc.

The diagnostic information and/or data obtained by instruments 130, 132, 152, and/or 175 are correlated or co-registered to angiographic image(s) and/or other two-dimensional or three-dimensional depictions of a patient's vasculature obtained by an external imaging system. In various embodiments, the diagnostic information obtained by the external imaging system can include externally-obtained angiographic images, x-ray images, CT images, PET images, MRI images, SPECT images, and/or other two-dimensional or three-dimensional extraluminal depictions of a patient's vasculature. Spatial co-registration can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. For example, a mechanical pullback device can be used to conduct the pressure-sensing procedure. The mechanical pullback device can move the pressure-sensing device through the vessel at a fixed, known rate. The location of the pressure measurements and/or the pressure ratio(s) can be determined based on the rate of the pullback and a known location of the pressure-sensing device (e.g., a start position, a mid-point position, an end position, available from angiography data). In some embodiments, diagnostic information and/or data is correlated to vessel images using techniques similar to those described in U.S. Provisional Patent Application No. 61/747,480, titled "SPATIAL CORRELATION OF INTRAVASCULAR IMAGES AND PHYSIOLOGICAL FEATURES" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety.

In some embodiments, diagnostic information and/or data is correlated to vessel images using techniques similar to those described in U.S. patent application Ser. No. 14/144,280, titled "DEVICES, SYSTEMS, AND METHODS FOR ASSESSMENT OF VESSELS" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety. In other embodiments, co-registration and/or correlation can be completed as described in International Application No. PCT/IL2011/000612, titled "CO-USE OF ENDOLUMINAL DATA AND EXTRALUMINAL IMAGING" and filed Jul. 28, 2011, which is hereby incorporated by reference in its entirety. Further, in some embodiments, co-registration and/or correlation can be completed as described in International Application No. PCT/IL2009/001089, titled "IMAGE PROCESSING AND TOOL ACTUATION FOR MEDICAL PROCEDURES" and filed Nov. 18, 2009, which is hereby incorporated by reference in its entirety. Additionally, in other embodiments, co-registration and/or correlation can be completed as described in U.S. patent application Ser. No. 12/075,244, titled "IMAGING FOR USE WITH MOVING ORGANS" and filed Mar. 10, 2008, which is hereby incorporated by reference in its entirety.

Figure 5:
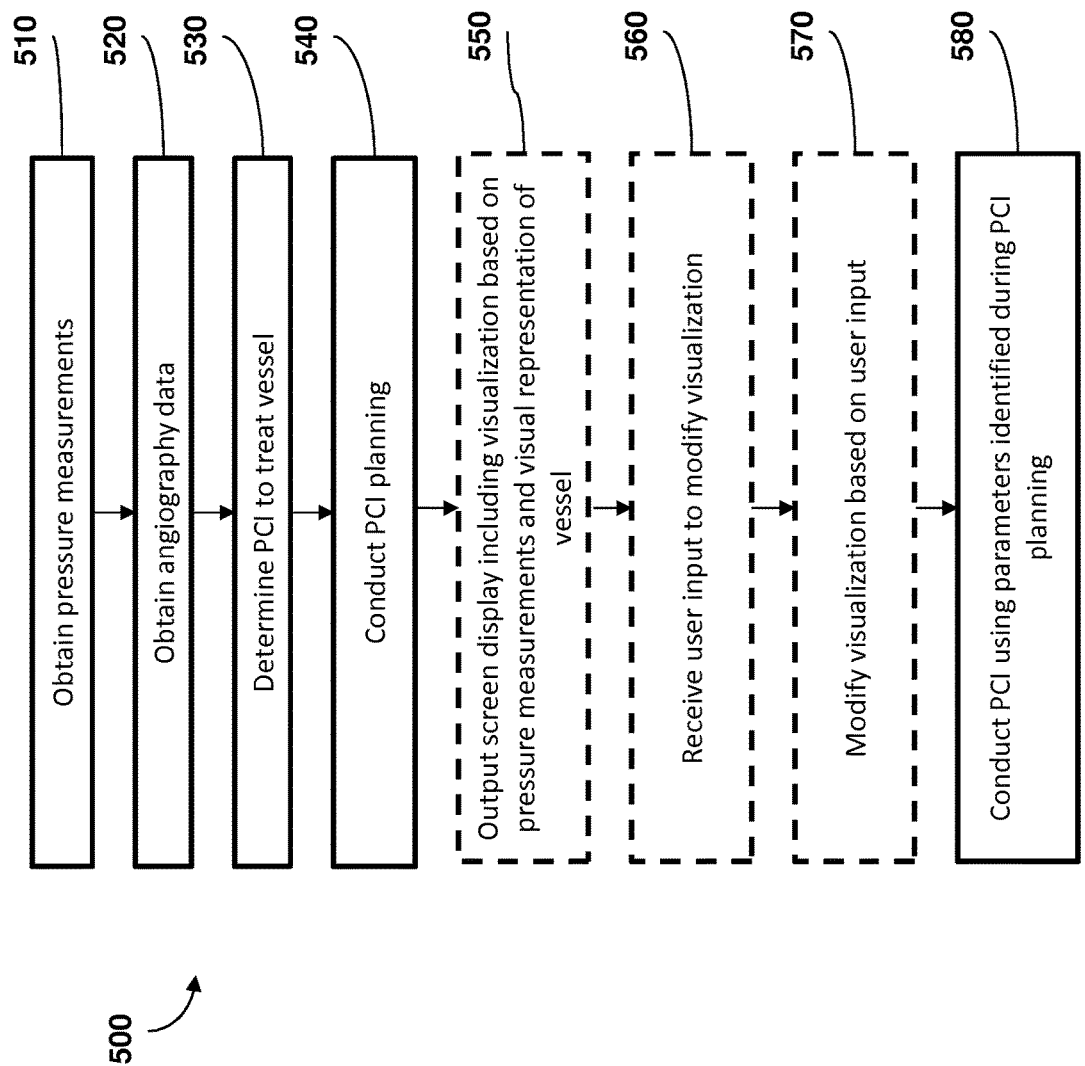
FIG. 5 is a flow diagram of a method of evaluating a vessel of a patient according to an embodiment of the present disclosure.

FIG. 5 is flowchart illustrating a method 500 of evaluating a vessel of a patient. The method 500 will be described in the context of a pressure-sensing procedure, such as an iFR, Pd/Pa, or FFR procedure. It is understood that the method 500 can be carried out in the context of a flow-sensing procedure, such as a CFR procedure. The method 500 can be better understood with reference to FIGS. 7, 9, 11, 13, 15, 17, 19, 21, 23, 25, and 27. At block 510, the method 500 includes obtaining pressure measurements. At block 520, the method 500 includes acquiring angiography data. In some embodiments, the pressure measurements are obtained simultaneously as the angiography data is acquired. Simultaneously collecting pressure measurements and angiography data can facilitate co-registration, as described above. For example, the collected pressure data can be co-registered such that the location of the pressure sensing component of the intravascular device within the vessel is known. A processing system can associate the location with the pressure measurements and/or the pressure ratio(s) at that location. The processing system can also generate a screen display including the pressure measurements and/or pressure ratios at their associated locations, as described with respect to block 530.

A clinician can insert pressure-sensing intravascular device(s), such as a catheter or guidewire, into the patient. In some embodiments, the clinician may guide the intravascular device within the patient to a desired position using the angiography data. After the pressure sensing intravascular device has been appropriately positioned in the patient, the clinician can initiate collection of pressure measurements. Pressure measurements can be collected during one or more of the following procedures: an FFR "spot" measurement where the pressure sensor stays in one place while hyperemia is induced; an FFR pullback in which an elongated period of hyperemia is induced and the sensor is pulled back to the ostium; an iFR "spot" measurement that is similar to the FFR spot measurement but without hyperemia; and an iFR pullback which is that the FFR pullback but without hyperemia. In various embodiments, physiological measurement collection can be carried through a combination of one or more of the procedures described above. Physiological measurement can be continuous, such as during a pullback procedure. Physiological measurements can occur while the intravascular device is moved in one direction. Measurement collection can be discontinuous procedure, such as when the intravascular device is selectively moved through the vessel (e.g., when movement of the intravascular device starts and stops, when the intravascular device is held at various points along the vessel longer than others, etc.). Physiological measurements can occur while the intravascular device is moved in both directions (e.g., proximally and distally within the blood vessel). Co-registration can be used to ensure that, regardless of how the physiological measurements were collected, the location of the measurement can be identified on an angiographic image of the vessel. For example, a composite of the collected physiological measurements can be generated based on the co-registered data.

In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

In typical embodiments, a processing system can collect raw pressure data from the intravascular device and process the data to compute pressure differential(s) or ratio(s). The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

Referring again to FIG. 5, at block 530, the method 500 includes determining PCI is the appropriate treatment for the vessel. Angiography data, pressure measurements, and/or other data can be used to determine that a vessel stenosis exists and that is it necessary to treat the vessel. Exemplary embodiments of determining to treat the vessel are described in U.S. Provisional Application No. 62/089,039, filed Dec. 8, 2014, the entirety of which is hereby incorporated by reference herein.

The method 500 includes, at step 540, planning the PCI. Planning the PCI can include interacting with a graphical user interface described herein to determine physiologic parameters for the PCI, such as stent position, stent length, stent diameter, etc. Using the screen displays described herein, a graphical representation of a stent positioned within a vessel can be visualized. The screen displays can include various co-registered physiologic data, such as pressure ratio(s), overlaid on the vessel at the location to which they are associated. The graphical representation of the stent can have various simulated or virtual properties, such as position, length, diameter, etc., such that it appropriately fits within the visual representation of the vessel. For example, the properties of the graphical representation of the stent can be manually selected by a clinician, e.g., based on user input, and/or automatically determined by a computing device. The properties of the graphical representation of the stent can be varied in response to a user input. As described with respect to block 580, real physiologic parameters for the PCI, such as stent position, stent length, stent diameter, etc., can be determined based on the simulated or virtual properties of the graphical representation of the stent. In this manner, angiographic data and physiology measurements can be combined in a meaningful way to plan and evaluate the outcome of the PCI. The therapy plan and any modifications to the stent parameters, as well as the predicted/anticipated outcome of the treatment, can be supported by collected data.

Planning the PCI (block 540) can include one or more of blocks 550, 560, and/570. At block 550, the method 500 includes outputting a screen display. The screen display includes a visualization based on the pressure measurements and a visual representation of the vessel. In some embodiments, the visual representation of the vessel is a two-dimensional or three-dimensional angiographic image of the vessel, such as an angiographic image generated based on angiography data collected at block 520. In some embodiments, visual representation of the vessel is two-dimensional or three-dimensional graphical representation of the vessel, such as a stylized image or reconstruction of the vessel. The visualization based on the pressure measurements can include numerical, graphical, textual, and/or other suitable visualizations. For example, the visualization can include one or more of a stent positioned within the visual representation of the vessel, calculated pressure ratio(s), markers indicative of a location within the vessel of the obtained pressure measurements or the calculated pressure ratio(s), a label identifying the vessel, among others. Visual representations of the vessel and visualizations based on the pressure measurements are described in the context of FIGS. 7-28. In some embodiments, the visualization based on the pressure measurements can include a heat map in which the visual representation of the vessel is colorized or otherwise gradated to shows changes in the obtained pressure measurements or calculated pressure ratio(s). Examples of screen displays including a heat map, calculated pressure ratios, markers indicative of a location associated with the obtained pressure measurements or the calculated pressure ratios, and other visualizations are described in U.S. Provisional Application No. 61/895,909, titled "Devices, Systems, and Methods for Vessel Assessment," and filed Oct. 25, 2013, the entirety of which is hereby incorporated by reference herein. In various embodiments, other collected data, computed quantities, etc., such as ECG waveforms, numerical values, can be provided on the screen display as described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Other exemplary screen displays are described in the discussion of method 600 (FIG. 6).

At block 560, the method 500 includes receiving a user input to modify the visualization. The user input can be to insert a stent into the visual representation of the vessel and/or move the stent within the vessel. The user input can be to change one or more characteristics of the stent, such as length, diameter, material, etc. For example, the user input can be to increase or decrease the length of the stent within the vessel. The user input can be received at a user interface device. In some embodiments, the user input is a touch input received at a touch sensitive display of a bedside controller. At block 570, the method 500 includes modifying the visualization based on the user input. For example, in response to the user input, a stent can be inserted into the visual representation of the vessel, the location of the stent within the vessel can be changed, and one or more characteristics of the stent (e.g., length, diameter, material, etc.) can be changed.

At block 580, the method 500 includes conducting the PCI using the physiologic parameters identified during the PCI planning. Real physiologic parameters (e.g., stent position, stent length, stent length, etc.) can be determined based on the position, length, diameter, etc., of the graphical representation of the stent within the visual representation of the vessel. For example, the computing device 172 can correlate the virtual/simulated characteristics of the graphical representation of the stent with the co-registered angiography data to determine the real physiologic parameters of the stent. For example, the length of the graphical representation of the stent can be correlated to an actual length within the vessel spanned by the stent using the angiographic image. In a similar manner, the position, diameter, and other virtual/simulated characteristics of the graphical representation of the stent can be correlated to corresponding, real physiologic parameters within the vessel using the angiographic image. In some embodiments, the dimensions of the vessel in the co-registered angiography data can be determined using quantitative coronary angiography (QCA), a known pullback speed, etc. The PCI can be carried out on the patient to treat the occluded vessel using a stent with the determined real, physiologic parameters.

Figure 6:
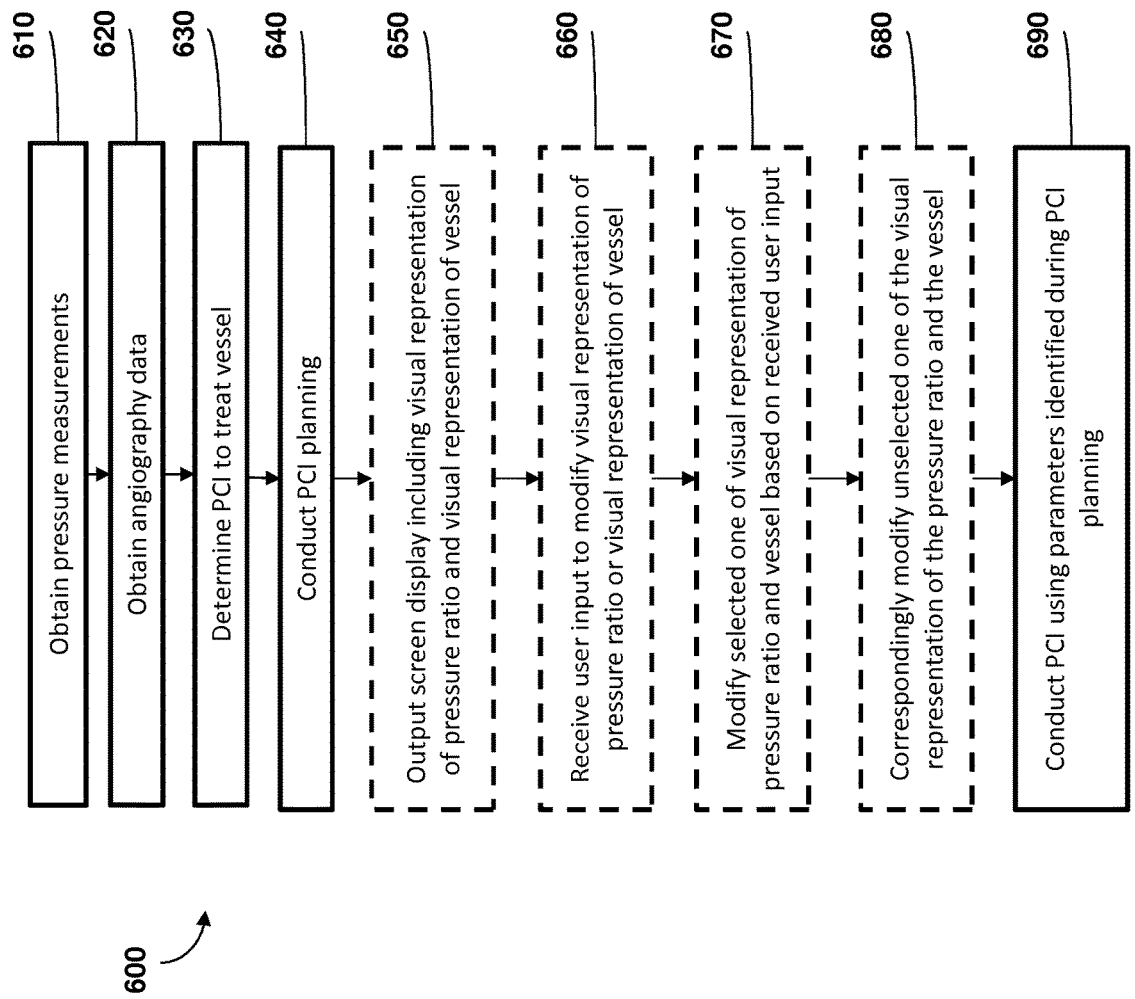
FIG. 6 is a flow diagram of a method of evaluating a vessel of a patient according to another embodiment of the present disclosure.

FIG. 6 is flowchart illustrating a method 600 of evaluating a vessel of a patient. The method 600 is similar to the method 500, and the method 600 will similarly be described in the context of a pressure-sensing procedure, such as an iFR, Pd/Pa, or FFR procedure. It is understood that the method 600 can be carried out in the context of a flow-sensing procedure, such as a CFR procedure. The method 600 can be better understood with reference to FIGS. 7-28. Blocks 610, 620, and 630 are similar to blocks 510, 520, and 530 of method 500, described above.

The method 600 includes, at step 640, planning the PCI. Planning the PCI can include interacting with a graphical user interface described herein to determine physiologic parameters for the PCI, such as stent position, stent length, stent diameter, etc. Using the screen displays described herein, a graphical representation of a stent positioned within a vessel or along a pressure curve can be visualized. The screen displays can include various co-registered physiologic data, such as pressure ratio(s), overlaid on the vessel or pressure curve at the location to which they are associated. The graphical representation of the stent can have various simulated or virtual properties, such as position, length, diameter, etc., such that it appropriately fits within the visual representation of the vessel. For example, the properties of the graphical representation of the stent can be manually selected by a clinician, e.g., based on user input, and/or automatically determined by a computing device. The properties of the graphical representation of the stent, can be varied in response to a user input. As described with respect to block 690, real physiologic parameters for the PCI, such as stent position, stent length, stent diameter, etc., can be determined based on the simulated or virtual properties of the graphical representation of the stent. In this manner, angiographic data and physiology measurements can be combined in a meaningful way to plan and evaluate the outcome of the PCI. The therapy plan and any modifications to the stent parameters, as well as the anticipated outcome of the treatment, can be supported by the collected angiography and/or pressure data.

Planning the PCI (block 640) can include one or more of blocks 650, 660, 670, and/or 680. At block 650, the method 600 includes outputting a screen display. The screen display includes a visual representation of a pressure ratio and a visual representation of vessel. In some embodiments, the screen display can include both the visual representation of the pressure ratio and the visual representation of the vessel, such as in a side by side configuration. In various embodiments, other collected data, computed quantities, etc., such as ECG waveforms, numerical values, can be provided on the screen display as described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Other exemplary screen displays are described in the discussion of method 500 (FIG. 5). As similarly described with respect to block 550, the visual representation of the vessel can include two-dimensional or three-dimensional angiographic image or graphical representation of the vessel.

The visual representation of the pressure ratio can include a graph of the calculated pressure ratio over time or relative to a location/position in the anatomy, such as the blood vessel. Exemplary embodiments of the visual representations of the pressure ratio are illustrated in FIGS. 8a, 8b, 10, 12, 14, 16, 18, 20, 22, 24, 26, and 28. The graph can show the pressure ratio calculated over the time of obtaining pressure measurements or relative to a location/position in the blood vessel, such as during a pullback. For example, the graph can show an iFR or FFR pressure ratio value. In that regard, the iFR pressure ratio may be calculated as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, filed Apr. 30, 2012 and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/856,509, filed Jul. 19, 2013 and titled "DEVICES, SYSTEMS, AND METHODS FOR ASSESSMENT OF VESSELS," and U.S. Provisional Patent Application No. 61/856,518, filed Jul. 19, 2013 and titled "DEVICES, SYSTEMS, AND METHODS FOR ASSESSING A VESSEL WITH AUTOMATED DRIFT CORRECTION," each of which is hereby incorporated by reference in its entirety.

It is understood that the visual representation of the pressure ratio can illustrate the pressure ratio and/or the underlying pressure measurements obtained by the multiple sensing components in any suitable way. Generally speaking, the representation of the data in the visual representation of the pressure ratio can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

At block 660, the method 600 includes receiving a user input to modify the visual representation of the pressure ratio or visual representation of the vessel. The user input can be to insert a stent into the visual representation of the vessel or the visual representation of the pressure ratio. The user input can be to move a stent within the vessel or along the visual representation of the pressure ratio. The user input can be to change one or more characteristics of the stent, such as length, diameter, material, etc. For example, the user input can be to increase or decrease the length of the stent within the vessel or along the visual representation of the pressure ratio. The user input can be received from a user interface device. In some embodiments, the user input is a touch input received at a touch sensitive display of a bedside controller. For example, a user input to modify the visual representation of the pressure ratio can be received directly on a graph of the pressure ratio over time. For example, a user input to modify the visual presentation of the vessel can be received directly on the angiographic image of the vessel.

At block 670, the method 600 includes modifying the selected one of the visual representation of the pressure ratio and the visual representation of the vessel. At block 680, the method 600 includes correspondingly modifying the unselected one of the visual representation of the pressure ratio and the visual representation of the vessel. For example, in response to a user input to modify the visual representation of the vessel, a stent can be inserted into the visual representation of the vessel. For example, the stent can be a graphical overlay positioned over an angiographic image of the vessel. A corresponding stent can also be inserted in the visual representation of the pressure ratio. Similarly, in response to a user input to modify the visual representation of the pressure ratio, a stent can be inserted along the graph of the pressure ratio over time. A corresponding stent can also be inserted into the visual representation of the vessel. The user directed modification and the automatic corresponding modification can be performed with various characteristics of a stent or other visualization. For example, the screen display can be modified to change the location of the stent along the visual representation of the pressure ratio, and the location of the stent within the vessel can be correspondingly changed and vice versa. One or more characteristics of the stent (e.g., length, diameter, material, etc.) can be changed on the visual representation of the pressure ratio, and the characteristic(s) can be correspondingly changed on the visual representation of the vessel and vice versa.

In some instances, one of the visual representation of the pressure ratio and the visual representation of the vessel can be better suited for PCI planning. One or more methods described herein allow for a clinician to use the visual representation that is best suited for the circumstances. For example, using the angiographic image may indicate that a stent of a particular length is sufficient to remedy the change in pressure as a result of a lesion in the vessel. However, because the pressure sensing device takes a relatively directly route through the vessel, the angiographic image may underestimate the actual length of the stent that is required. In contrast, the visual representation of the pressure ratio may more accurately suggest a length of the stent required to address the pressure drop. Thus, a screen display of the visual representation of the pressure ratio can be modified to include a stent that has an increased length. The visual representation of the vessel can be correspondingly modified to include the longer stent. In other embodiments, the visual representation of the vessel can provide a more accurate info for PCI planning and corresponding changes can be made on the visual representation of the pressure ratio.

At block 690, the method 600 includes conducting the PCI using the physiologic parameters identified during the PCI planning. Real physiologic parameters (e.g., stent position, stent length, stent length, etc.) can be determined based on the position, length, diameter, etc., of the graphical representation of the stent within the visual representation of the vessel and/or along the pressure curve. For example, the computing device 172 can correlate the characteristics of the graphical representation of the stent with the co-registered angiography data to determine the real physiologic parameters of the stent. For example, the length of the graphical representation of the stent can be correlated to an actual length within the vessel spanned by the stent using the angiographic image or a known distance within the vessel between data points (e.g., pressure ratios) on the pressure curve. In a similar manner, the position, diameter, and other virtual/simulated characteristics of the graphical representation of the stent can be correlated to corresponding, real physiologic parameters within the vessel using the angiographic image or known dimensions within the vessel between data points (e.g., pressure ratios) on the pressure curve. In some embodiments, the dimensions of the vessel in the co-registered angiography can be determined using quantitative coronary angiography (QCA), a known pullback speed, etc. The PCI can be carried out on the patient to treat the occluded vessel using a stent with the determined real, physiologic parameters.

The discussion below generally refers to FIGS. 7-28. FIGS. 7-28 are exemplary screen displays (or partial screen displays) according to embodiments of the present disclosure. FIGS. 7, 9, 11, 13, 15, 17, 19, 21, 23, 25, and 27 illustrate screen displays including a visual representation of a vessel. FIGS. 8*a*, 8*b*, 10, 12, 14, 16, 18, 20, 22, 24, 26, and 28 illustrate screen displays including a visual representation of the pressure ratio. FIGS. 7-28 can be displayed on a display device of system assessing a patient's vasculature, such as the display device 180 associated with computing device 172 (FIG. 4). That is, one or more components (e.g., a processor and/or processing circuit) of the system (e.g., computing device 172) can provide display data to cause the images of FIGS. 7-28 to be shown on a display device (e.g., display device 180). The pressure ratio values illustrated in FIGS. 7-28 are exemplary.

Figure 7:
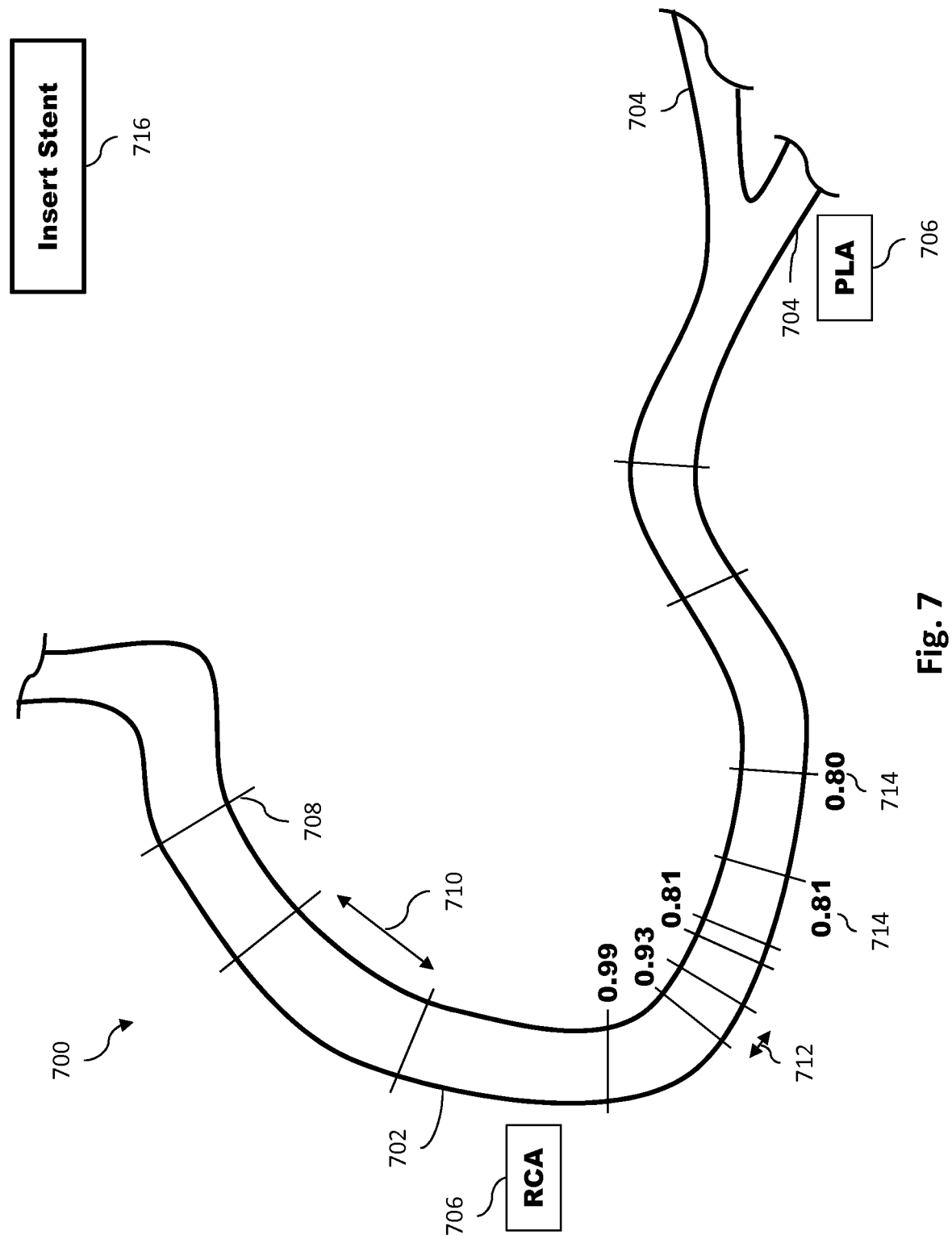
FIG. 7 is a screen display according to an embodiment of the present disclosure.
Figure 8A:
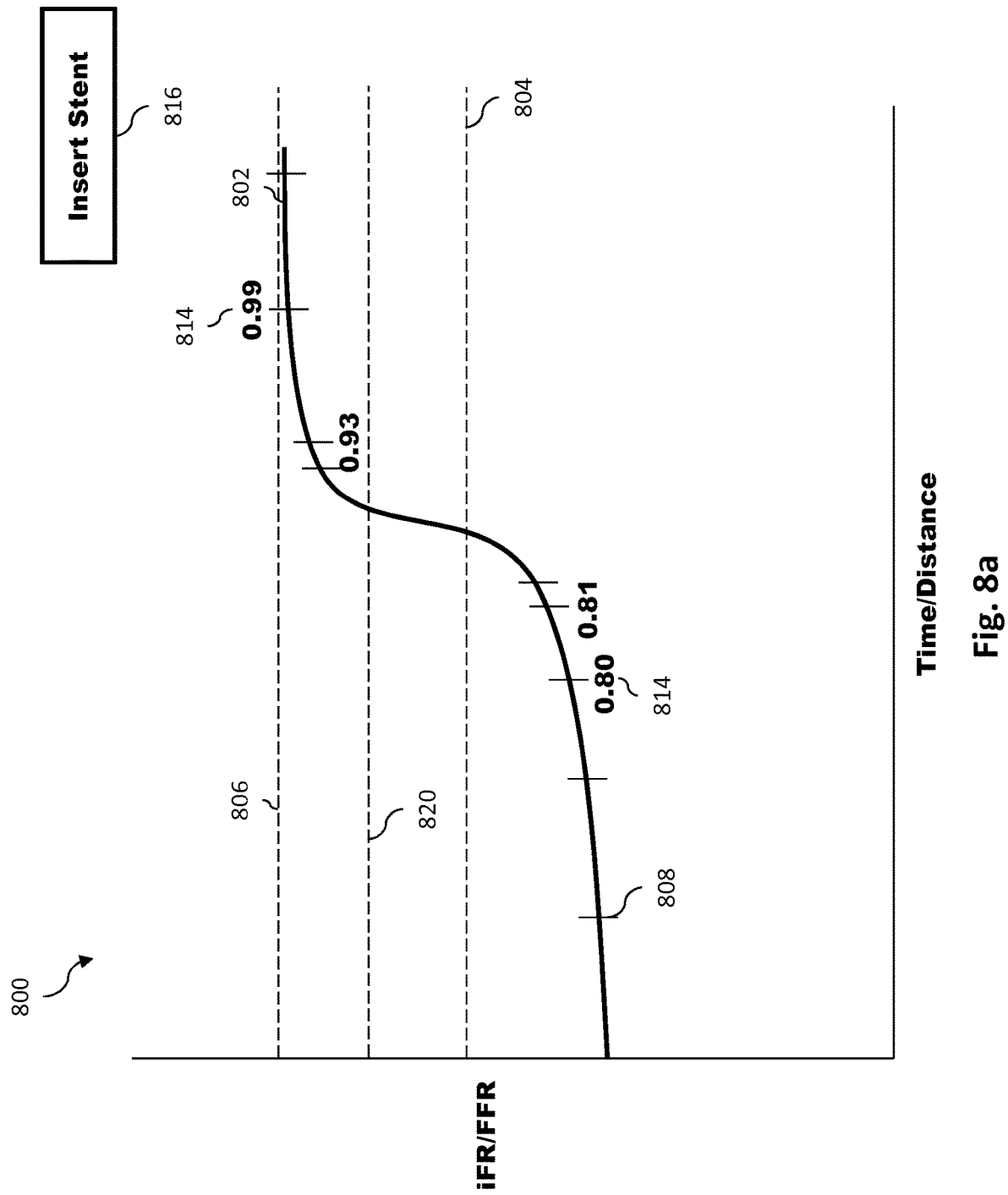
FIG. 8a is a screen display according to another embodiment of the present disclosure.
Figure 8B:
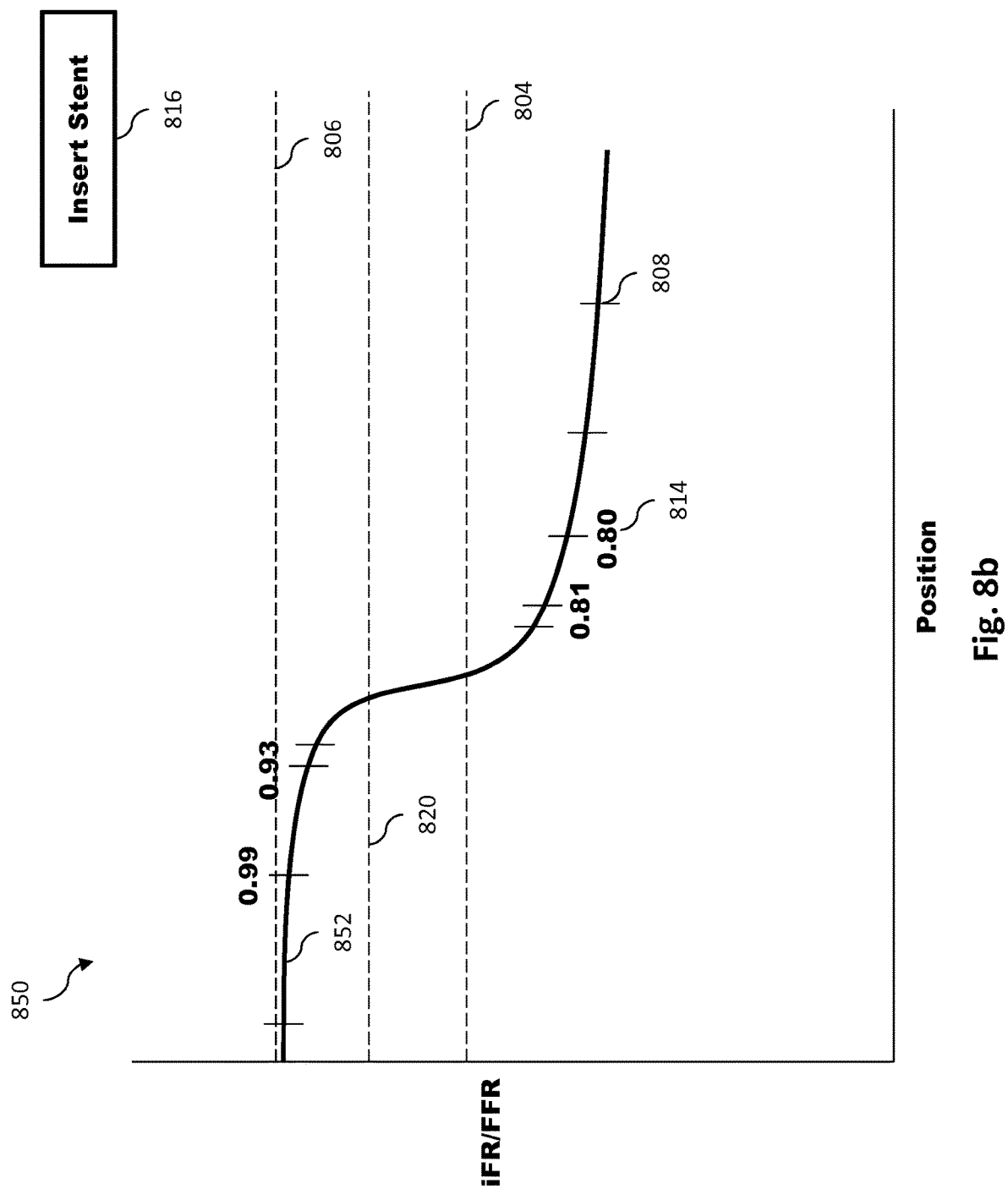
FIG. 8b is a screen display according to another embodiment of the present disclosure.

FIG. 7 illustrates a screen display 700 (or partial screen display) including a visual representation of a vessel. The data depicted in the screen display 700 (FIG. 7) corresponds to the data shown in screen displays 800 and 850 (FIGS. 8*a* and 8*b*). The screen display includes a visual representation of a vessel 702 into which an intravascular device having a pressure sensing component is guided. Angiographic and pressure data can be collected with the intravascular device within the vessel 702. For example, the pressure data can be collected during a pullback procedure, which in the embodiment of FIG. 7 is from the right to the left of the vessel 702. The collected angiography data can be used to generate an angiographic image including the vessel 702 and other branch vessels 704. The one or more visualizations described herein can be a graphical overlay on the angiographic image. The screen display 700 includes label fields 706 identifying the particular vessel(s). In some embodiments, a computing device (e.g., computing device 172 of FIG. 4) uses the angiography data, such as the contours, location, branches, and other features of the vessel(s) to automatically identify the vessel. The position and/or viewing angle of the external imaging system (e.g., angiography or x-ray system) can also be used to identify the vessel. A computing device can generate the display data associated with the labels 706, including alphabetical, numerical, alphanumeric, and/or symbolic characters. In the embodiment of FIG. 7, the labels 706 include an abbreviation of the identified vessel, such as "RCA" for right coronary artery and "PLA" for postero-lateral artery. While abbreviations and particular vessels are used in FIG. 7, it is understood that any suitable label can be used. In some embodiments, a user can selectively activate or deactivate one or more of the labels 706 such that a portion, all, or none of the labels 706 are included in the screen display 700.

The screen display 700 also includes markers 708 indicative of a location within the vessel 700 associated with the collected pressure measurements or computed pressure ratio. For example, the markers 708 can be a location of the pressure sensor when the pressure measurements are collected. In the embodiment of FIG. 7, the markers 708 are line segments that transect the vessel 702. Other examples of markers indicative of location are described in U.S. Provisional Application No. 61/895,909, titled "Devices, Systems, and Methods for Vessel Assessment," and filed Oct. 25, 2013, the entirety of which is hereby incorporated by reference herein. In one embodiment, such as during an iFR procedure, one pressure ratio is computed per heartbeat cycle. Thus, each marker 708 is indicative of collected data and/or computed pressure ratio during the heartbeat cycle. In some embodiments, a user can selectively activate or deactivate one or more of the markers 708 such that a portion, all, or none of the markers 708 are included in the screen display 700. The markers 708 can be separated by varying distances within the vessel 702, as indicated by distances 710 and 712. In turn, the distances 710 and 712 can correspond to the speed through which the pressure sensing device is guided through the vessel 702. In embodiments in which the pressure sensing device is guided through the vessel 702 at a constant speed, the distance between the markers 708 is equal or nearly equal such that successive markers 702 are positioned at equal or nearly equal intervals. In the embodiments in which the pressure sensing device is guided through the vessel 702 at a non-constant speed, the distance between the markers 708 will vary to a greater extent such that successive markers 708 are positioned at unequal intervals. For example, the pressure sensing device can be slowed down near an obstruction such that data from a relatively greater number of heartbeat cycles is collected. As illustrated in FIG. 7, there is less distance between successive markers 708 around a pressure change attributable to an obstruction in the vessel 702. Co-registration can be implemented such that the location of the pressure sensing intravascular device within the vessel 702 is known during each heartbeat cycle. As a result, the pressure sensing intravascular device can be guided through the vessel 702 (e.g., during a pullback procedure) with a non-constant speed such that the pace of data collection in the vessel 702 can be controlled by the clinician. For example, the clinician can slow down for more information near a clinically significant portion of the vessel 702 such as a lesion. For example, the clinician can speed up through non-clinically significant portions of the vessel 702.

The pressure change in the vessel 702 is indicated by the pressure ratio fields 714. The pressure ratio fields are provided adjacent the markers 708. In the embodiment of FIG. 7, only a portion of the pressure ratio fields 714 are shown.

In various embodiments, a portion, all, or none of the pressure ratio fields 714 can provide the computed pressure ratio associated with a given location. For example, a user can selectively activate or deactivate one or more of the pressure ratio fields 714. In various embodiments, the pressure ratio fields 714 include alphabetical, numerical, alphanumeric, and/or symbolic characters. In FIG. 7, the fields 714 include are numeric values associated with an iFR calculation. In other embodiments, the fields 714 can include an "FFR," "iFR," "Pd/Pa," or other label to identify the type of quantity being displayed. Such embodiments are described, for example, in U.S. Provisional Application No. 61/895,909, titled "Devices, Systems, and Methods for Vessel Assessment," and filed Oct. 25, 2013, the entirety of which is hereby incorporated by reference herein. A pressure change is indicated by the values in the fields 714. For example, in FIG. 7, an obstruction in the vessel 702 likely exists between the values 0.93 and 0.81.

Figure 9:
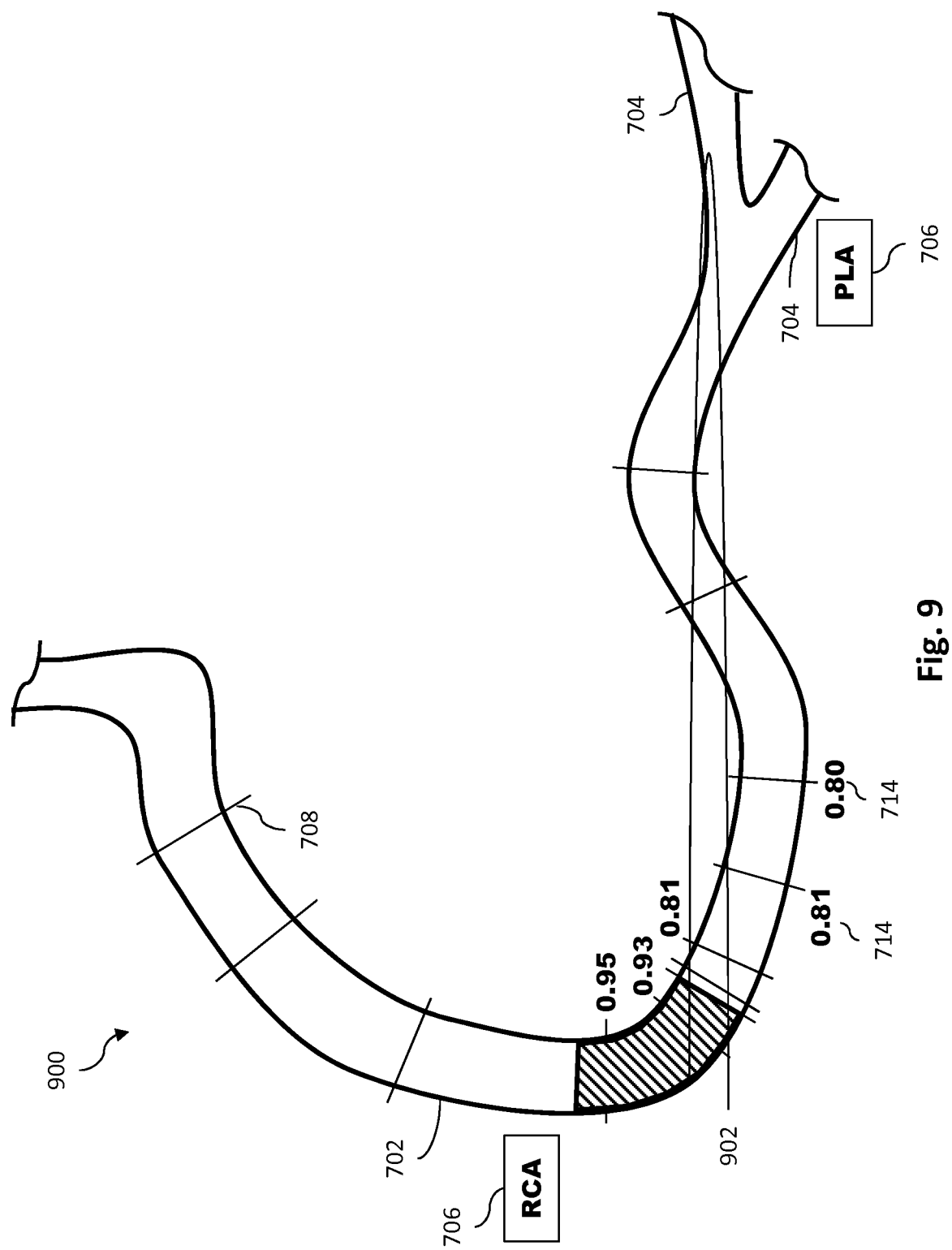
FIG. 9 is a screen display according to another embodiment of the present disclosure.

The screen display 700 additionally includes an insert stent field 716. Selection of the insert stent field 716 can be a user input to modify the visual representation of the vessel and/or a visualization based on the pressure measurements. In some embodiments, selection of the insert stent field 716 can cause a computing device (e.g., computing device 172) to determine one or more recommended characteristics of a stent to be deployed within the vessel 702, including position, diameter, length, material, etc. The determination of the one or more characteristics can be based on the collected pressure data, computed pressure ratio(s), angiography data, a threshold pressure ratio, a target pressure ratio, an ideal pressure ratio, etc. In that regard, the stent can be described as a visualization based on pressure measurements. For example, the characteristics, such as the position and length, of the stent can be selected to remedy a drop in the pressure ratio across an obstruction. The computing device can determine the characteristics of the stent and generate display data to cause a stent to be displayed within the vessel 702 (as illustrated in FIG. 9). As described below, a clinician can modify the recommended characteristics of the stent. In some embodiments, selection of the insert stent field 716 provides a stent without determining its characteristics based on the collected pressure data, computed pressure ratio(s), and/or angiography data. In this manner, a clinician can customize the characteristics of the stent. For example, a clinician can provide a user input (such as a click and drag, or other suitable input) along the vessel 702, and computing device can provide a graphical representation of a stent having the length corresponding to the distance traversed by the user input along the vessel 702. In some embodiments, a plurality of stent options can be provided when the insert stent field 716 is selected, as described in greater detail with respect to FIG. 25.

FIGS. 8a and 8b illustrate screen displays 800 and 850 (or partial screen displays) including a visual representation of a pressure ratio. The data depicted in the screen displays 800 and 850 (FIGS. 8a and 8b) corresponds to the data shown in screen display 700 (FIG. 7). The screen displays 800 and 850 include curves 802, 852 respectively of the pressure ratios within the vessel 702. The curves 802, 852 are representative of the same data, except that the x-axes are different. The screen display 800 (FIG. 8a) includes time or distance on the x-axis and a pressure ratio quantity (such as iFR, FFR, Pd/Pa, etc.) on the y-axis. For example, in the embodiment shown in FIG. 7, a moving pressure sensing device can be guided from right to left within the vessel 702 during the pullback procedure while a fixed pressure sensing device remains stationary on the left side of the vessel 702. Values along the x-axis of screen display 800 can correspond to the duration of a pullback procedure and/or distance traveled by the moving pressure sensing device during the pullback procedure. The screen display 850 includes position corresponding to the physical orientation of the vessel 702 along the x-axis and a pressure ratio quantity (such as iFR, FFR, Pd/Pa, etc.) on the y-axis. That is, the screen display 850 shows the pressure ratios associated with the left side of the vessel 702 on the left side of the curve 852 and the pressure ratios associated with the right side of the vessel 702 on the right side of the curve 852. In some instances, providing a pressure ratio plot that corresponds to the physical location along the vessel can facilitate easier PCI planning. The discussion below generally refers to the screen display 850, but it is understood that the screen display 800 can be equivalently utilized.

The screen displays 800 and 850 include an ideal pressure ratio line 806. The ideal line 806 is representative of a pressure ratio equal to one (1), which is indicative of a vessel with no obstructions. Physiologically, a pressure ratio equal to one (1) is the maximum possible pressure ratio and occurs when proximal and distal pressure measurements are equal. During PCI planning, a clinician tries to determine stent parameters that will cause a patient's pressure ratios to return as closely as possible to the ideal line 806.

The screen displays 800 and 850 include a threshold pressure ratio 804. The threshold 804 can be set at a value indicative of transition between pressure ratios representative of a healthy vessel and pressure ratios representative of a vessel having an obstruction. Pressure ratios above the threshold 804 can be representative of a vessel for which treatment is not recommended, and pressure ratios below the threshold 804 can be representative of a vessel for which treatment is recommended. The threshold 804 can vary depending on the pressure ratio scale (e.g., iFR, FFR, Pd/Pa, etc.) used in the screen displays 800 and 850. For example, the threshold 804 for FFR can be 0.80, and the threshold 804 for iFR can be 0.89. For example, if a vessel has FFR values above 0.80, the clinician can determine not to treat the vessel. If the vessel has FFR values below 0.80, the clinician can determine to treat the vessel with a PCI.

The screen displays 800 and 850 include a target line 820. The target line 820 can correspond to a pressure ratio value that is associated with clinically beneficial outcomes for the patient. The target line 820 can correspond to a pressure ratio value higher than the threshold 804 in some embodiments. That is, the threshold 804 can represent a minimum pressure ratio value that can be considered healthy, while the target line 820 can represent a higher pressure ratio value that is associated with efficacious treatment. The target line 820 can vary depending on the pressure ratio scale (e.g., iFR, FFR, Pd/Pa, etc.) used in the screen displays 800 and 850. For example, the target line 820 for FFR can be 0.93. The graphical user interface for PCI planning can allow the clinician to set the pressure ratio value for the threshold 804 and/or the target line 820. For example, the clinician can access settings options that allow for modification of the threshold 804 and/or the target line 820. One of the goals during insertion of a stent during a PCI is to return, as closely as possible, the actual pressure ratio values of the curves 802 and 852 to the value indicated by the ideal line 806. However, it may not be medically possible to recreate perfect flow within the stenosed vessel. In such circumstances, the target line 820 represents a medically acceptable pressure ratio values that are indicative of efficacious treatment. Thus, during PCI planning, the clinician determines stent parameters to return the patient's pressure ratio values to as close to the ideal line 806 as possible and at least above the target line 820. The threshold 804, the target line 820, and/or the ideal line 806 can be selectively provided on the screen displays 800 and 850, in response to a user input to show/hide the visualizations. While the threshold 804 and the target line 820 are shown in FIGS. 10, 12, 14, 16, 18, 20, 22, 24, 26, and 28, it is understood that none or any one or more the threshold 804, the target line 820, and/or the ideal line 806 can be provided on the screen displays.

In some embodiments, various colors and/or other visual indicators are provided on the screen displays 800 and 850 to indicate a difference between the threshold 804 and the actual pressure ratio. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

The screen displays 800 and 850 additionally include markers 808 and pressure ratio fields 814. The markers 808 and pressure ratio fields 814 are similar to those described in the context of FIG. 7. While the curves 802 and 852 are depicted as continuous in FIGS. 8*a* and 8*b*, the markers 808 can be representative of actual data points on the curves 802 and 852. The values of the curves 802 and 852 between the markers 808 can be interpolated based on the pressure ratios associated with the markers 808. A computing device (e.g., computing device 172 of FIG. 4) can provide data processing, data interpolation, smoothing, and perform other computations to generate the pressure ratio curves 802 and 852. The ideal pressure ratio line 806, the threshold 804, markers 808, and pressure ratio fields 814 can be selectively activated and deactivated such that a portion, all, or none appear the screen displays 800 and 850.

The screen displays 800 and 850 additionally include an insert stent field 816. Selection of the insert stent field 816 can be a user input to modify the visual representation of the pressure ratio. As similarly described with respect to FIG. 7, in some embodiments, selection of the insert stent field 816 can cause a computing device (e.g., computing device 172 of FIG. 4) to determine one or more recommended characteristics of a stent to be deployed along the curves 802 or 852, including the stent position, diameter, length, material, etc. The determination of the one or more characteristics can be based on the collected pressure data, computed pressure ratio(s), angiography data, a threshold pressure ratio, a target pressure ratio, an ideal pressure ratio, etc. In that regard, the stent can be described as a visualization based on pressure measurements. For example, the characteristics, such as the position and length, of the stent can be selected to span a drop in the pressure ratio curve. The computing device can determine the characteristics of the stent and generate display data to cause a stent to be displayed along the curves 802 and 852 (as illustrated in, e.g., FIG. 10). As described below, a clinician can modify the recommended characteristics of the stent. In some embodiments, selection of the insert stent field 816 provides a stent without determining its characteristics based on the collected pressure data, computed pressure ratio(s), and/or angiography data. In this manner, a clinician can customize the characteristics of the stent. For example, a clinician can provide a user input (such as a click and drag, or other suitable input) along the curves 802 and/or 852, and computing device can provide a graphical representation of a stent having the length corresponding to the distance traversed by the user input along the curves 802 and/or 852. In some embodiments, a plurality of stent options can be provided when the insert stent field 816 is selected, as described in greater detail with respect to FIG. 26.

Figure 10:
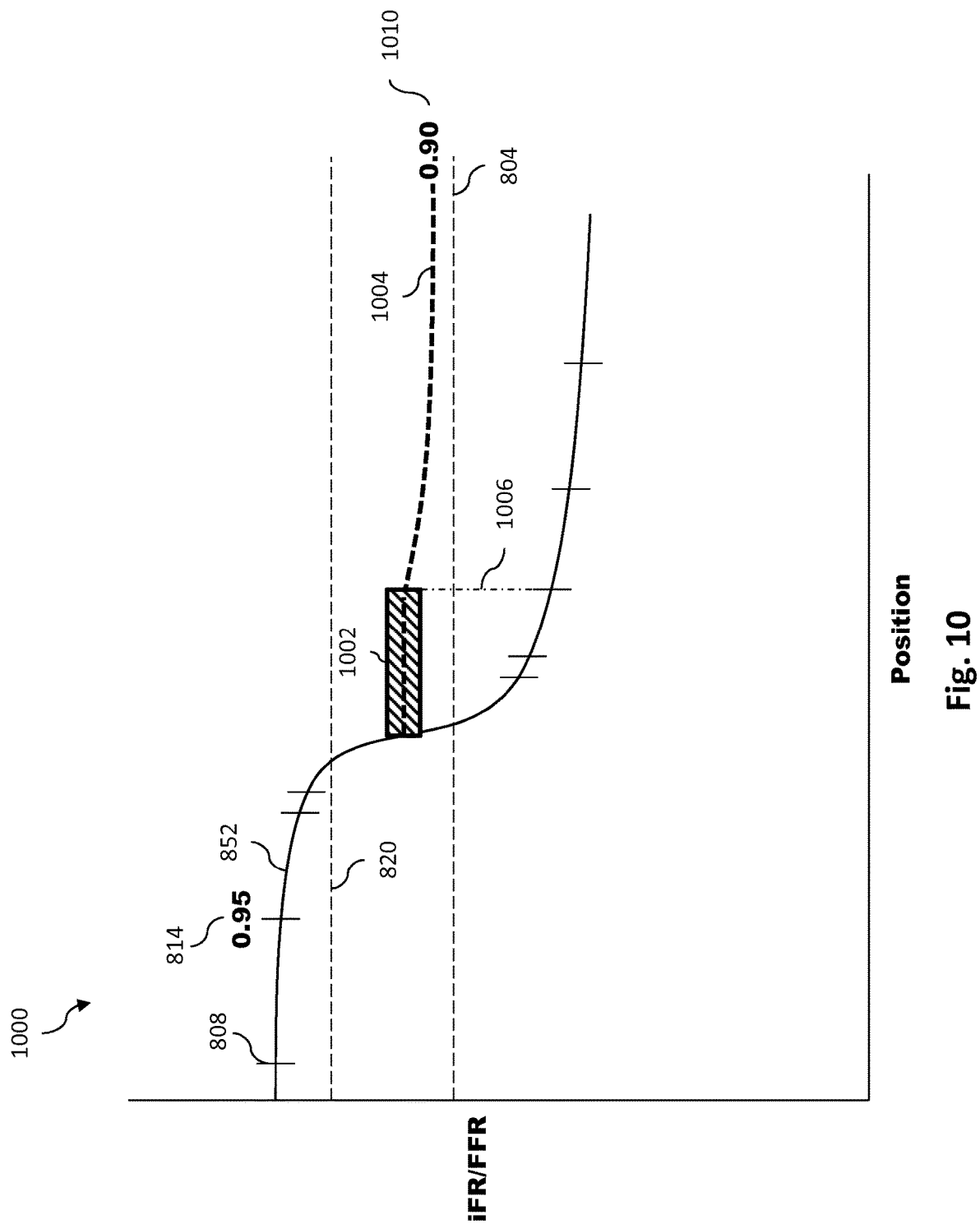
FIG. 10 is a screen display according to another embodiment of the present disclosure.

FIG. 9 illustrates a screen display 900 (or partial screen display) including a visual representation of a vessel. The data depicted in the screen display 900 (FIG. 9) corresponds to the data shown in screen display 1000 (FIG. 10). A graphical representation of a stent 902 is positioned in the visual representation of the vessel 702. The stent 902 can be inserted into the vessel in response to a user input to modify the visual representation of the vessel and/or modify a visualization based on the pressure measurements. As described above, the location, length, diameter, material, and/or other characteristics can be automatically generated by a computing device and corresponding display data can be provided to a display device. For example, the diameter of the stent can be auto-sized to match the diameter of the vessel in the angiographic image. The image characteristics of the stent 902 that determine how the stent 902 appears in the screen display 900 can be chosen such that the stent 902 is visually distinguishable within the vessel 702. The image characteristics can include a color, shading, pattern, transparency, borders, and other related characteristics. In some embodiments, the image characteristics of the stent 902 are selected to match the physical appearance of an actual stent. In some embodiments, the image characteristics of the stent 902 are selected to highlight a region within the vessel 702 in which the stent is inserted. Real physiologic values for a stent to be positioned within an occluded vessel of a human patient can be determined based on the location, length, diameter, material, and/or other virtual/simulated characteristics of the graphical representation of the stent 902.

FIG. 10 illustrates a screen display 1000 (or partial screen display) including a visual representation of a pressure ratio. The data depicted in the screen display 1000 (FIG. 10) corresponds to the data shown in screen display 900 (FIG. 9). A graphical representation of a stent 1002 is positioned along the visual representation of the pressure ratio curve 852. The characteristics of the graphical representation of stent 1002, such as the position and length, among others, correspond to the characteristics of the graphical representation of stent 902 that is positioned within the vessel 702 (FIG. 9). The stent 1002 can be inserted along the pressure ratio curve 852 in response to a user input to modify the visual representation of the pressure ratio and/or modify a visualization based on the pressure measurements. As described above, the location, length, diameter, material, and/or other physical characteristics can be automatically generated by a computing device and corresponding display data can be provided to a display device. The image characteristics of the stent 1002 that determine how the stent 1002 appears in the screen display 100 can be chosen such that the stent 1002 is visually distinguishable along the curve 852. The image characteristics can include a color, shading, pattern, transparency, borders, and other related characteristics. In some embodiments, the image characteristics of the stent 1002 are selected to match the physical appearance of an actual stent. In some embodiments, the image characteristics of the stent 1002 are selected to highlight a region along the curve 852 where the stent is inserted. Real physiologic values for a stent to be positioned within an occluded vessel of a human patient can be determined based on the location, length, diameter, material, and/or other virtual/simulated characteristics of the graphical representation of the stent 1002.

The screen display 1000 includes corrected pressure curve 1004. The corrected pressure curve 1004 represents the anticipated changes to pressure curve 852 as a result of the deployment of the stent 1002, at the current location and with the current characteristics, such as length. No change in the pressure is expected across the length of the stent 1002, as illustrated in the corrected pressure curve 1004. That is, placement of the stent 1002 is ideally creating perfect or near perfect flow across that portion of the vessel 702. An end of the stent 1002 can be indicated by a stent end notation 1006. In different embodiments, various other graphical representations of the stent end can be utilized. The stent end notation 1006 can be selectively provided to the screen display 1000, e.g., based on a user input to show/hide the visualization. The stent end notation 1006 is representative of the point beyond which the corrected pressure curve 1004 is expected to behave like the pressure curve 852. As shown, the corrected pressure curve 1004 is shaped similar to the pressure curve 852, past the stent end notation 1006. However, the pressure values indicated by the corrected pressure curve 1004 are higher as a result of the stent 1002 correcting at least a portion of the pressure drop across a lesion in the vessel.

Screen display 1000 additionally includes a corrected pressure ratio value 1010. The corrected pressure ratio value 1010 can correspond to the numerical value of the corrected pressure ratio curve 1004. One or both of the corrected pressure ratio value 1010 and the corrected pressure ratio curve 1004 can provide a clinician validation that the selected treatment will achieve the clinical goal of reducing pressure loss in the vessel. For example, the threshold 804 can correspond to an iFR value of 0.89, above which vessels can be characterized as healthy. If the corrected pressure ratio value 1010 provides an iFR value that is greater than 0.89 (as it does in the embodiment of FIG. 10), the clinician can understand that the placement of the stent with the given parameters (e.g., length, diameter, position, etc.) will provide some benefit in treating the vessel. The clinician can also understand that the proposed stent parameters do not result in the corrected pressure ratio curve 1004 or the corrected pressure ratio value 1004 equaling or exceeding the target line 820, at which clinical benefits are likely to result from the therapeutic intervention. Thus, the clinician can vary the stent parameters, as described herein, to move the stent, modify the stent length, etc., to plan a PCI that results in a corrected pressure ratio that exceeds the target line 820. In some embodiments, a clinician can make a medical determination that it is infeasible for the corrected pressure ratio curve 1004 to reach the target line 820 and that treatment to raise the corrected pressure ratio curve 1004 above the threshold 804 is sufficient. The corrected pressure ratio value 1010 can be associated with the distal portion of the corrected pressure ratio curve 1004 (e.g., the distal most value, an average of values of the corrected pressure ratio curve, etc.). The corrected pressure ratio value 1010 can be provided adjacent corrected pressure ratio curve 1004. The corrected pressure ratio value 1010 can be selectively provided in response to a user input to show/hide the visualization.

A computing device (e.g., computing device 172) can compute the values of the corrected pressure curve 1004 based on the obtained pressure measurements, calculated pressure ratios, target pressure ratio, ideal pressure ratio, etc. The corrected pressure curve 1004 can be computed and provided in real time such that the curve 1004 is adjusted based on modifications to the location and length of the stent 1002, among other physical characteristics, made by a clinician. The clinician can modify the physical characteristics of the stent so that the values of the corrected pressure curve are as close to being equal to an ideal pressure ratio (such the ideal pressure ratio line 806 of FIG. 8*b*) and/or at least greater than a target pressure ratio (such as the target line 820 of FIG. 8*b*).

In some embodiments, inserting a graphical representation of a stent in the vessel 702 of the screen display 900 (FIG. 9) can cause a graphical representation of a stent to be correspondingly inserted along the pressure ratio curve 852 of the screen display 1000 (FIG. 10). Similarly, inserting a stent along the pressure ratio curve 852 of the screen display 1000 (FIG. 10) can cause the stent to be correspondingly inserted in the vessel 702 of the screen display 900. In this manner, a clinician can conduct PCI planning while interacting directly with a selected one of the screen displays 900 and 1000, while automatically viewing corresponding changes in the unselected one of the screen displays 900 and 1000.

Figure 11:
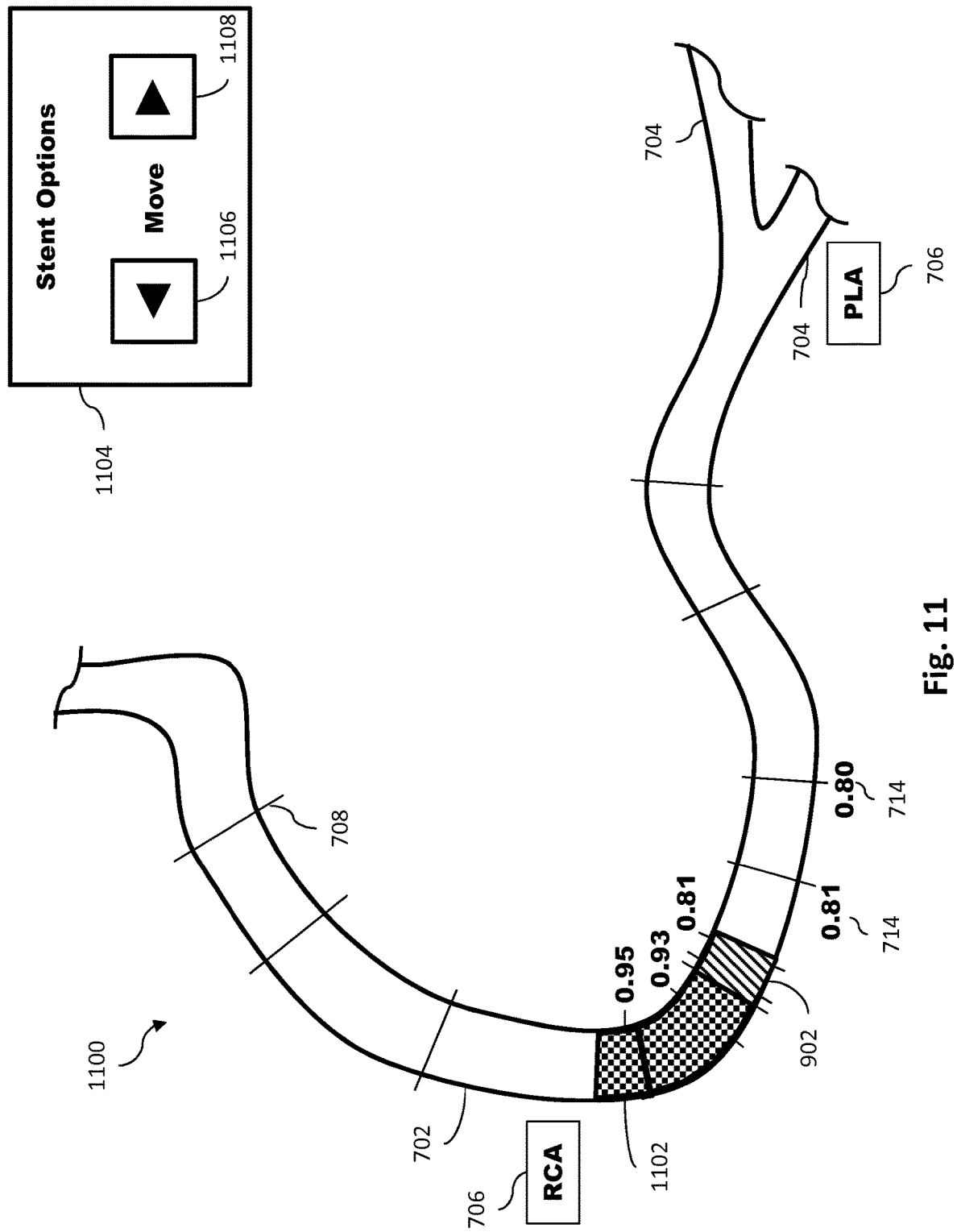
FIG. 11 is a screen display according to another embodiment of the present disclosure.
Figure 12:
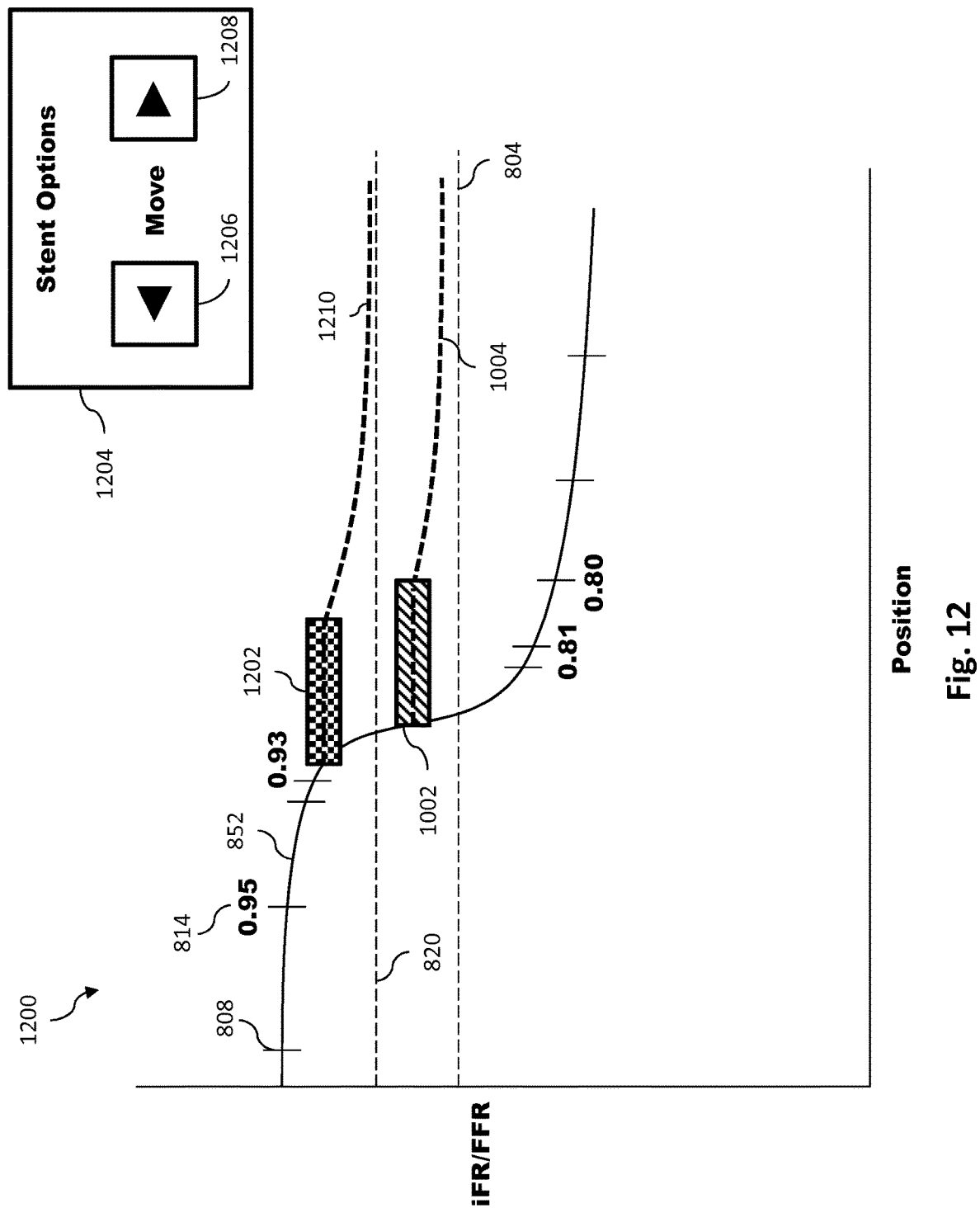
FIG. 12 is a screen display according to another embodiment of the present disclosure.
Figure 13:
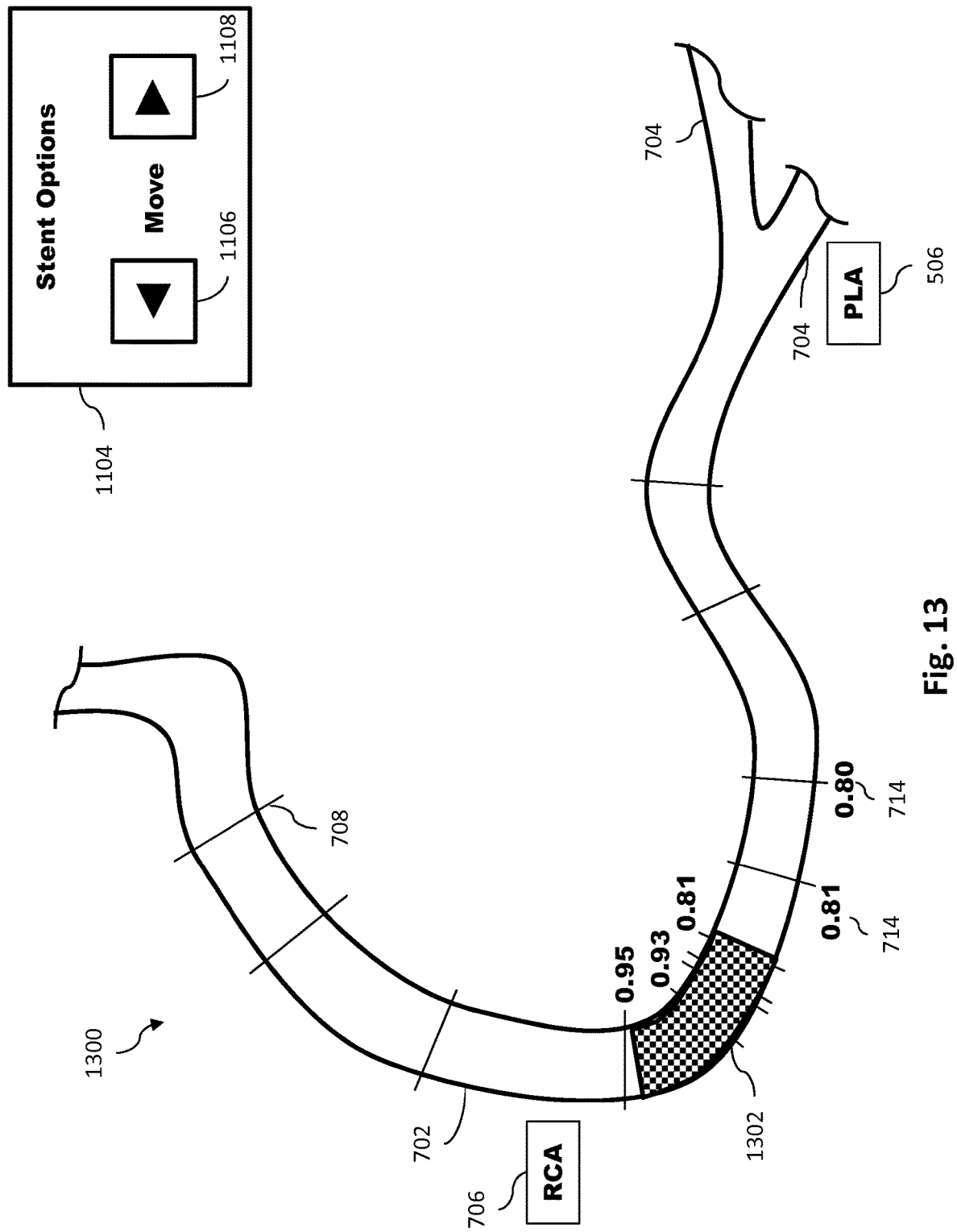
FIG. 13 is a screen display according to another embodiment of the present disclosure.
Figure 14:
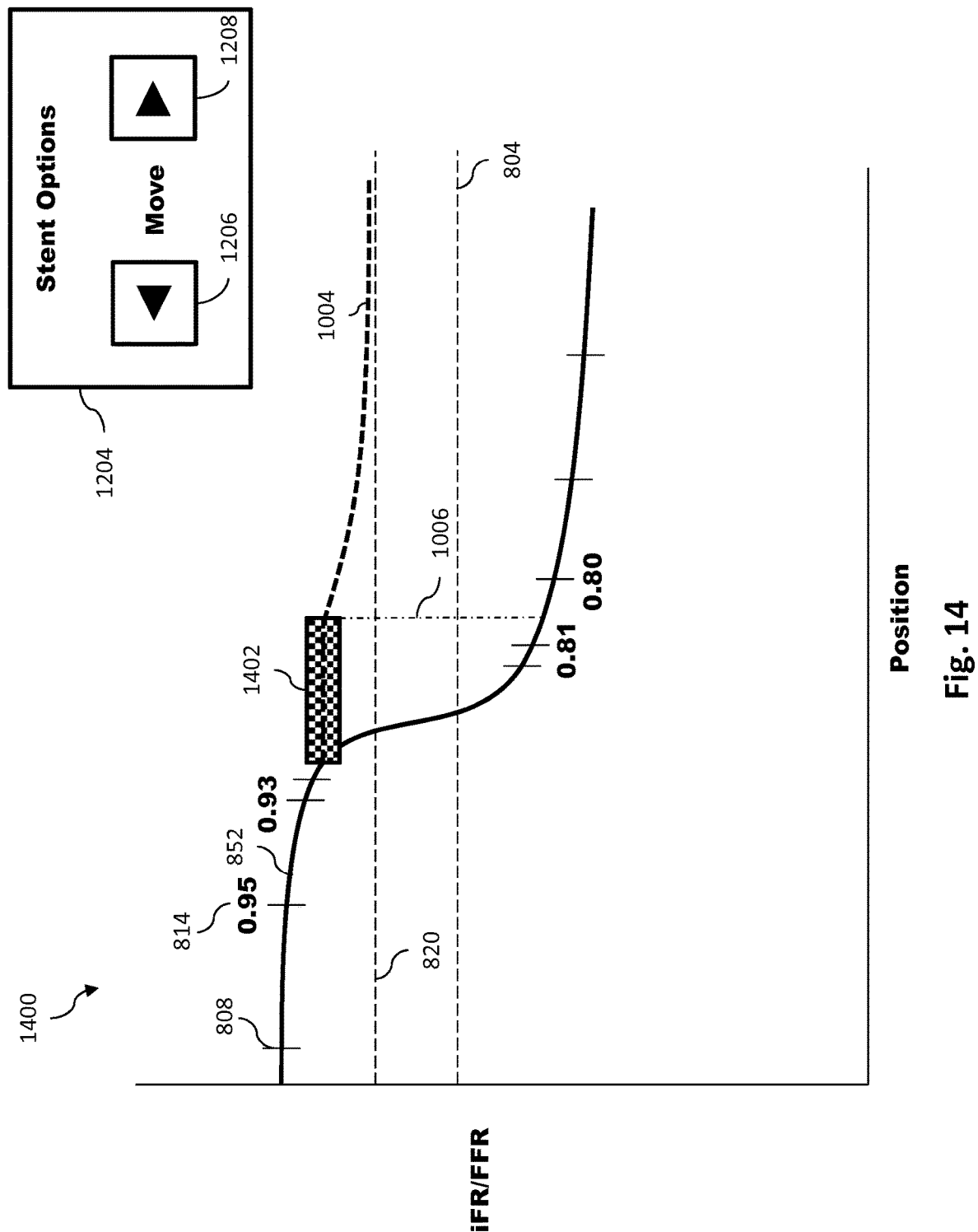
FIG. 14 is a screen display according to another embodiment of the present disclosure.

FIGS. 11-14 describe movement of a stent within the vessel and along a pressure ratio curve. FIG. 11 illustrates a screen display 1100 (or partial screen display) including a visual representation of a vessel. The data depicted in the screen display 1100 (FIG. 11) corresponds to the data shown in screen display 1200 (FIG. 12). The graphical representation of the stent 902 can be moved within the vessel 702. That is, the position of the stent 902 with the vessel 702 can be changed in response to a user input to move the stent 902. The user input to move the stent 902 can be described as a user input to modify a visualization based on the pressure ratio or a visual representation of the vessel. In some embodiments, a stent options menu 1104 can provide options 1106 and 1108 to move the stent 902 to the left or to the right within the vessel 702. In some embodiments, such as when the screen display 1100 is provided on a touch-sensitive display, a user can use one or more touch inputs on the stent 902 itself to move the stent within the vessel 702. For example, a user can touch and drag the stent 902 to a different position. In the embodiment of FIG. 11, the screen display 1100 is shown to be in an intermediate stage in which the stent 902 is being moved to the left to a new position 1102 in response to a corresponding user input. Screen display 1300 of FIG. 13 shows the stent 1302 at the new position in the vessel 702. The data depicted in the screen display 1300 (FIG. 13) corresponds to the data shown in screen display 1400 (FIG. 14).

FIG. 12 illustrates a screen display 1200 (or partial screen display) including a visual representation of a pressure ratio. The data depicted in the screen display 1200 (FIG. 12) corresponds to the data shown in screen display 1100 (FIG. 11). The graphical representation of the stent 1002 can be moved along the pressure ratio curve 852. That is, the position of the stent 1002 along the curve 852 can be changed in response to a user input to move the stent 1002. The user input to move the stent 1002 can be described as a user input to modify a visualization based on the pressure ratio or a visual representation of the pressure ratio. In some embodiments, a stent options menu 1204 can provide options 1206 and 1208 to move the stent 1002 to the left or to the right along the curve 852. In some embodiments, such as when the screen display 1200 is provided on a touch-sensitive display, a user can use one or more touch inputs on the stent 1002 itself to move the stent along the curve 852. For example, a user can touch and drag the stent 1002 to a different position. In the embodiment of FIG. 12, the screen display 1200 is shown to be in an intermediate stage in which the stent 1002 is being moved to the left to a new position 1202 in response to a corresponding user input. In some embodiments, the corrected pressure ratio curve 1004 can be updated in real time such that, as the stent 1002 is being moved, the curve 1004 is adjusted to reflect the predicted pressure ratio with the stent 1002 in the contemporaneous position. Screen display 1400 of FIG. 14 shows the stent 1402 at the new position along the curve 852. The data depicted in the screen display 1400 (FIG. 140) corresponds to the data shown in screen display 1300 (FIG. 13). Screen display 1400 also provides a corrected pressure ratio curve 1004 that is updated based on the new position of the stent 1402. For example, the curve 1004 of FIG. 14 is above the target line 820, which is indicative of that fact that the stent 1402 is better positioned (compared to the original position of the stent 1002 in FIG. 12) relative to an obstruction in the vessel 702 to remedy the changes in pressure caused by the obstruction. A corrected pressure ratio curve 1004 at least above the target line 820 can be a goal of the clinician during PCI planning. In response to the selected virtual/simulated characteristics of the stent 1402, the computing device predicts that the goal will be reached based on the collected pressure data. The virtual/simulated characteristics of the stent 1402 can be correlated to real, physiological parameters of a stent to be positioned within the human vessel to treat a patient based on the PCI planning. Thus, movement of the graphical representation of the stent allows a clinician to choose an appropriate physiologic location for stent deployment to maximize clinical efficacy during PCI planning.

In some embodiments, moving the stent in the vessel 702 of the screen display 1100 (FIG. 11) can cause the stent to be correspondingly moved along the pressure ratio curve 852 of the screen display 1200 (FIG. 12). Similarly, moving a stent along the pressure ratio curve 852 of the screen display 1200 (FIG. 12) can cause the stent to be correspondingly moved in the vessel 702 of the screen display 1100 (FIG. 11). In this manner, a clinician can conduct PCI planning while interacting directly with a selected one of the screen displays 1100 and 1200, while automatically viewing corresponding changes in the unselected one of the screen displays 1100 and 1200. For example, a clinician can work directly on the screen display 1200 that illustrates the pressure ratio curve 852 and the positioning of the stent relative to the pressure ratio curve. The stent can be moved along the pressure ratio curve 852 such that the corrected pressure ratio curve 1004 more closely matches or exceeds the target line 820. A corresponding change in the position of the stent can be made on the screen display 1100 (FIG. 11) of the vessel such that a clinician understands where the stent should be deployed in the vessel to achieve the corrected pressure ratio curve.

Figure 15:
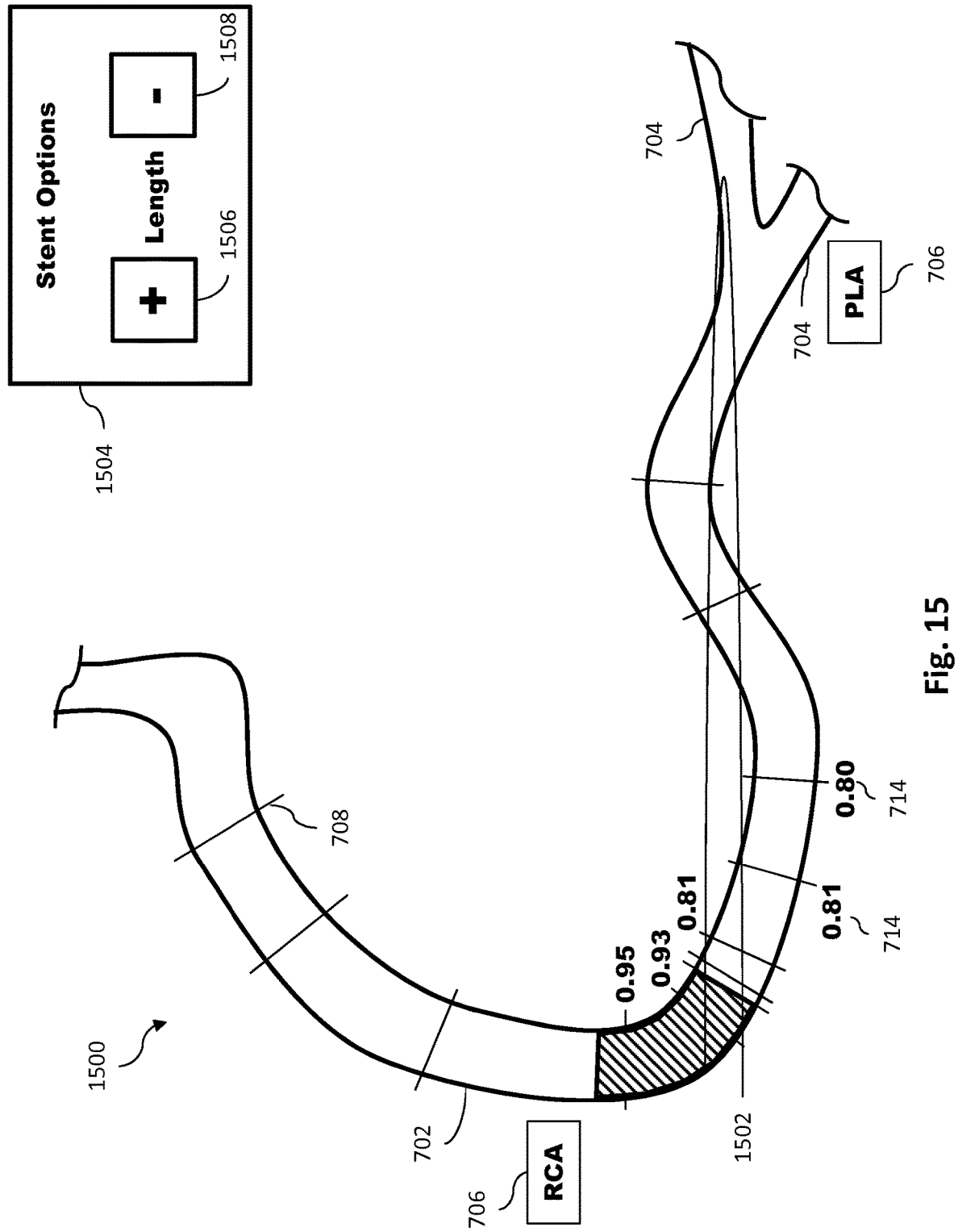
FIG. 15 is a screen display according to another embodiment of the present disclosure.
Figure 16:
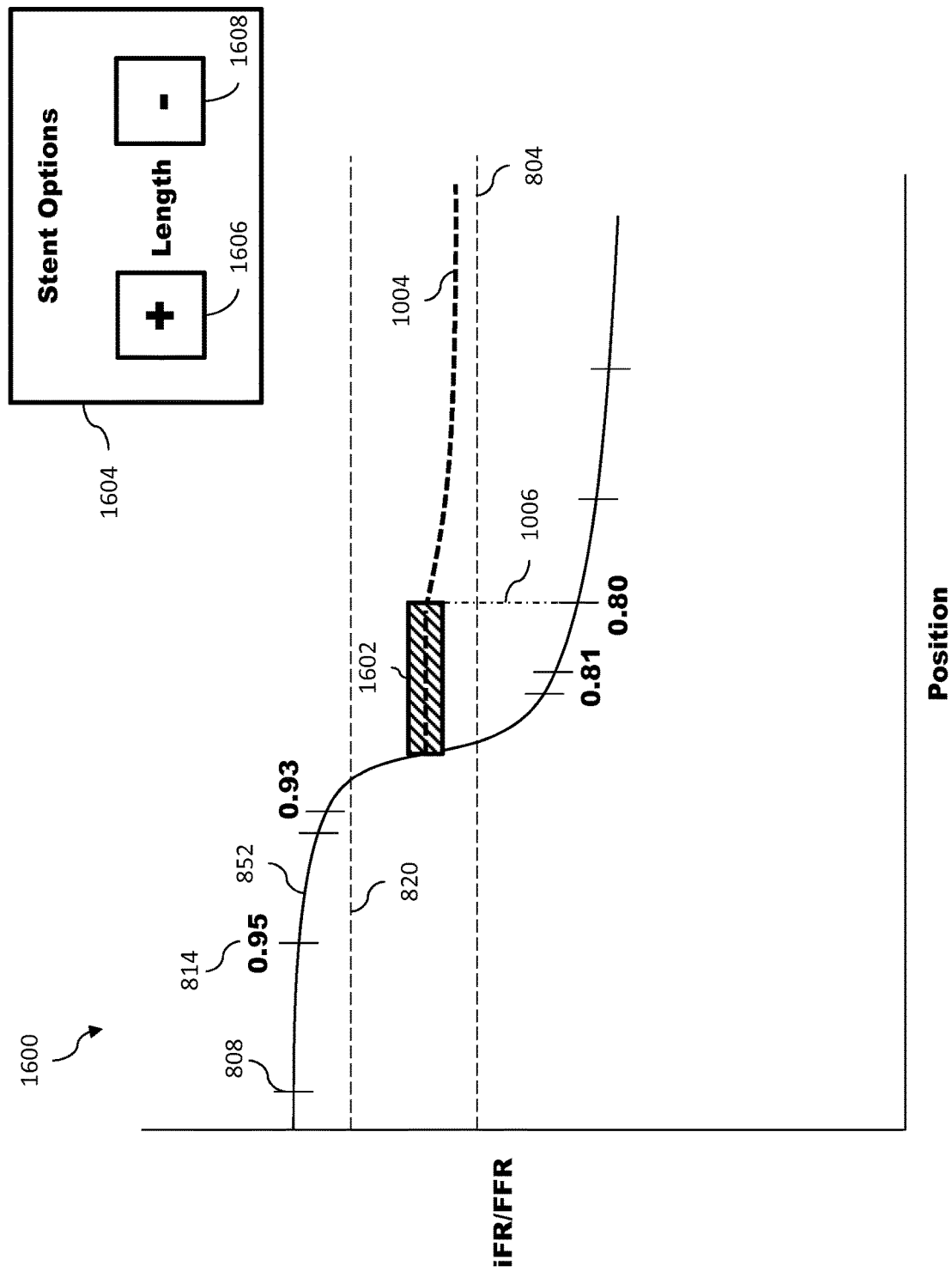
FIG. 16 is a screen display according to another embodiment of the present disclosure.

FIGS. 15-24 describe changing the length of a stent within the vessel and along a pressure ratio curve. In particular, FIGS. 17-20 describe shortening a stent, and FIGS. 21-24 describe lengthening a stent. FIG. 15 illustrates a screen display 1500 (or partial screen display) including a visual representation of a vessel. The data depicted in the screen display 1500 (FIG. 15) corresponds to the data shown in screen display 1600 (FIG. 16). The length of the graphical representation of the stent 1502 can be decreased or increased within the vessel 702. That is, the stent 1502 within the vessel 702 can be shortened or lengthened in response to a user input to shorten or to lengthen the stent 1502, respectively. The user input to shorten or lengthen the stent 1502 can be described as a user input to modify a visualization based on the pressure ratio or a visual representation of the vessel. In some embodiments, a stent options menu 1504 can provide options 1506 and 1508 to increase or decrease, respectively, the length of the stent 1502. In some embodiments, such as when the screen display 1500 is provided on a touch-sensitive display, a user can use one or more touch inputs on the stent 1502 itself to change the length of the stent within the vessel 702. For example, a user can touch and drag one, the other, or both of the ends of the stent 1502 (as described in greater detail with respect to FIGS. 17 and 21). FIG. 15 illustrates the stent 1502 before a user input to change the length of the stent is received.

FIG. 16 illustrates a screen display 1600 (or partial screen display) including a visual representation of a pressure ratio. The data depicted in the screen display 1600 (FIG. 16) corresponds to the data shown in screen display 1500 (FIG. 15). The length of the stent 1602 can be increased or decreased along the pressure ratio curve 852. That is, the stent 1602 along the curve 852 can be shortened or lengthened in response to a user input to shorten or lengthen the stent 1602, respectively. The user input to shorten of lengthen the stent 1602 can be described as a user input to modify a visualization based on the pressure ratio or a visual representation of the pressure ratio. In some embodiments, a stent options menu 1604 can provide options 1606 and 1608 to increase or decrease, respectively, the length of the stent 1602. In some embodiments, such as when the screen display 1600 is provided on a touch-sensitive display, a user can use one or more touch inputs on the stent 1602 itself to change the length of the stent along the curve 852. For example, a user can touch and drag one, the other, or both of the ends of the stent 1602 (as described in greater detail with respect to FIGS. 18 and 22). FIG. 16 illustrates the stent 1602 before a user input to change the length of the stent is received.

Figure 17:
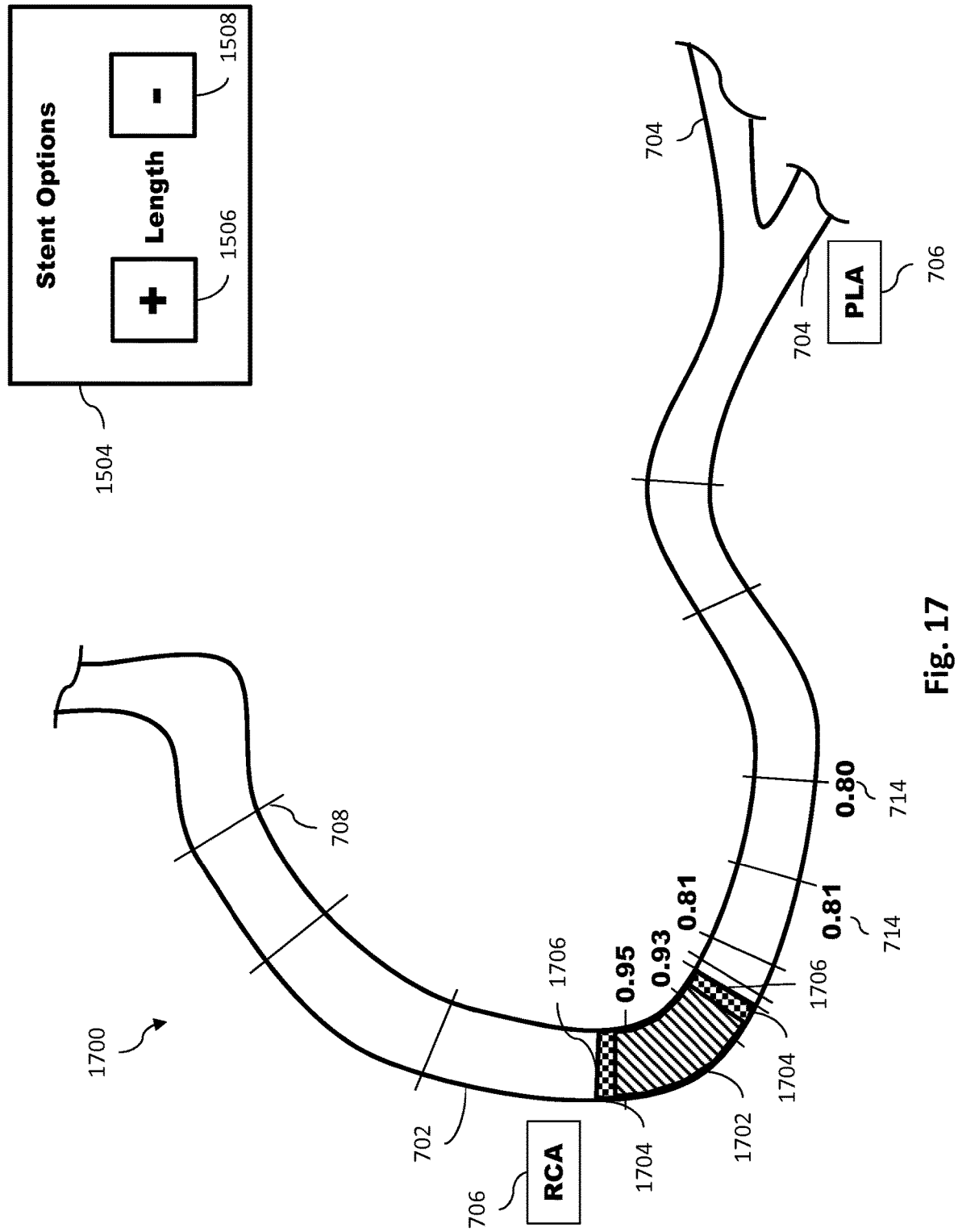
FIG. 17 is a screen display according to another embodiment of the present disclosure.
Figure 18:
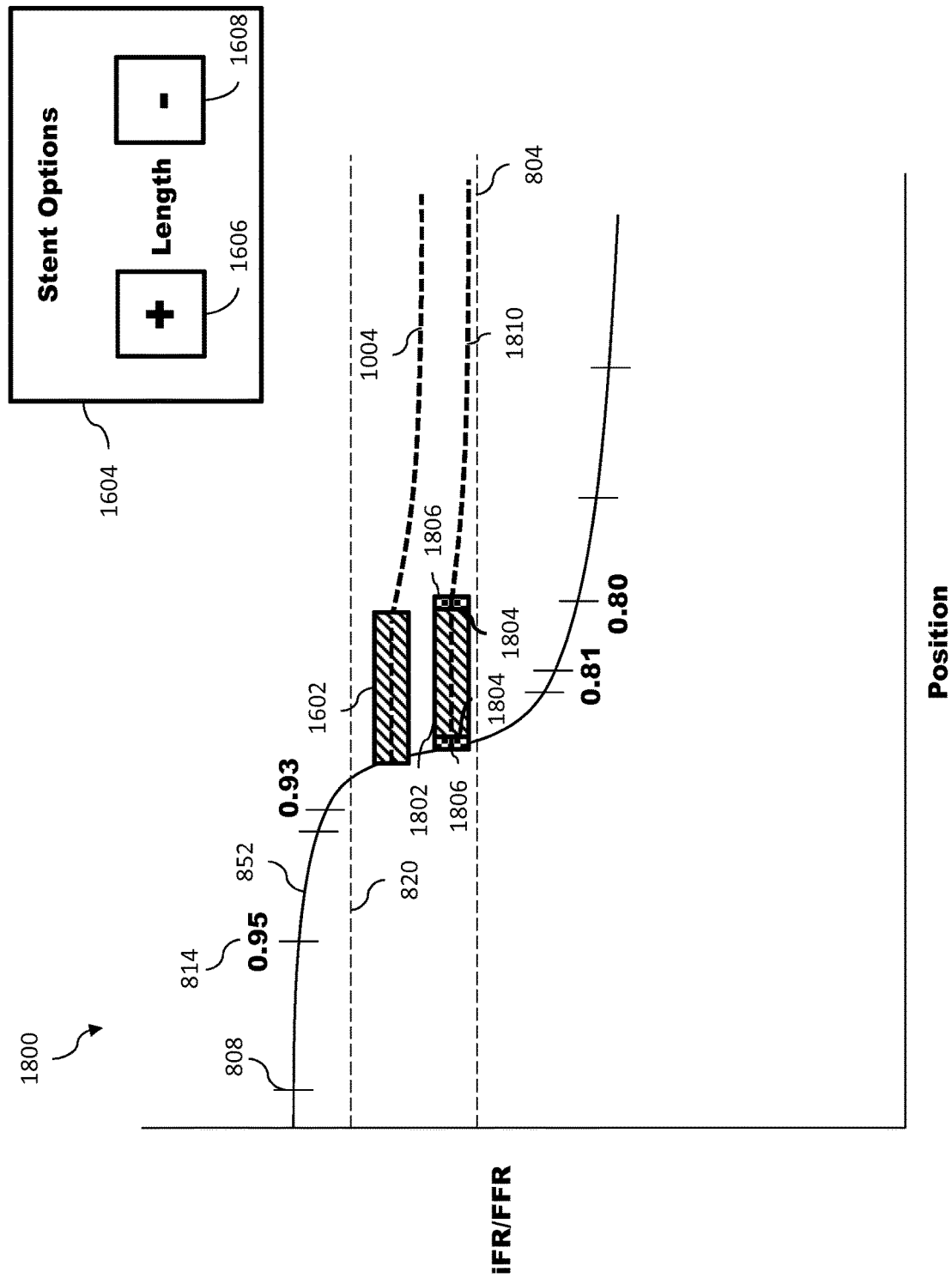
FIG. 18 is a screen display according to another embodiment of the present disclosure.
Figure 19:
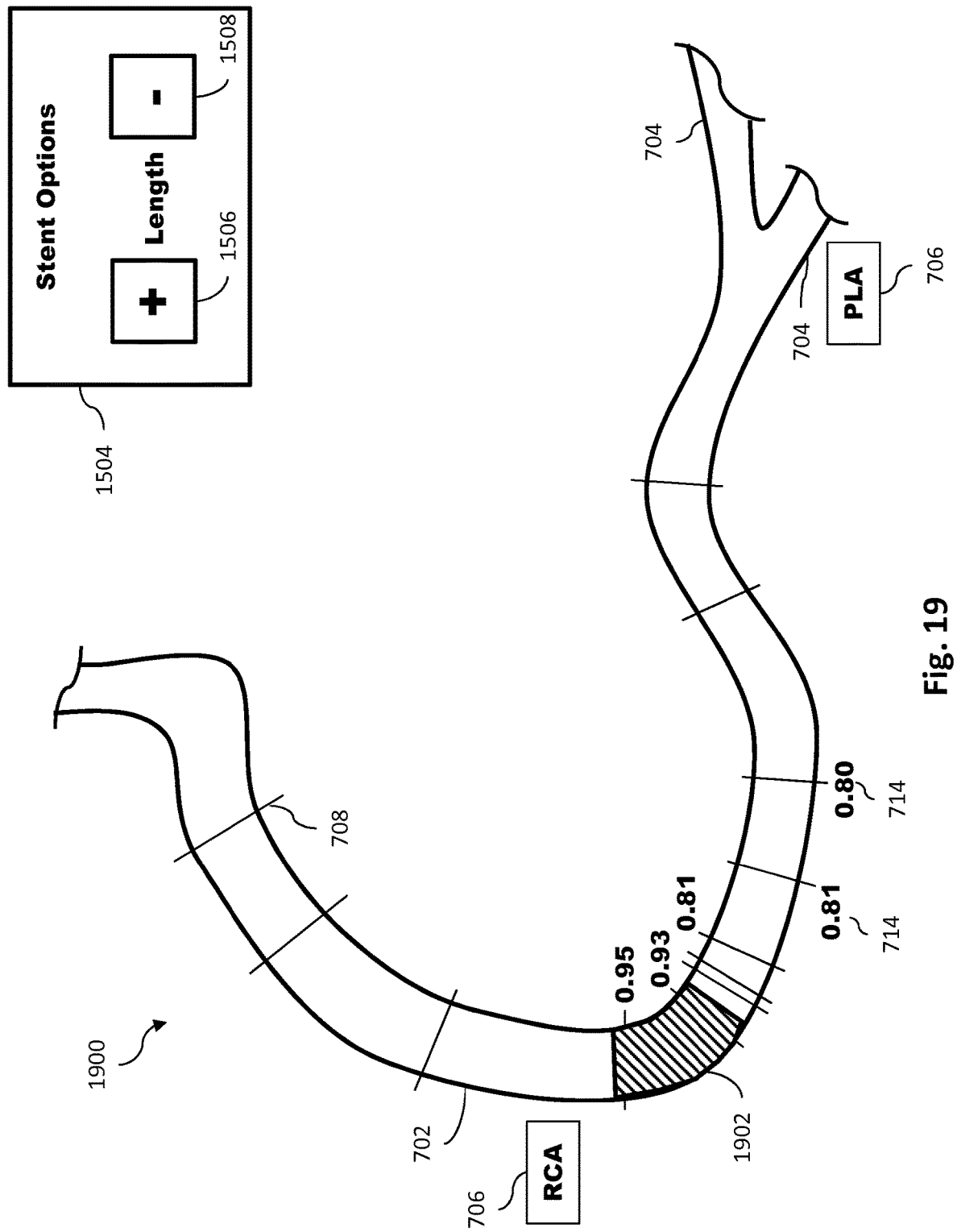
FIG. 19 is a screen display according to another embodiment of the present disclosure.
Figure 20:
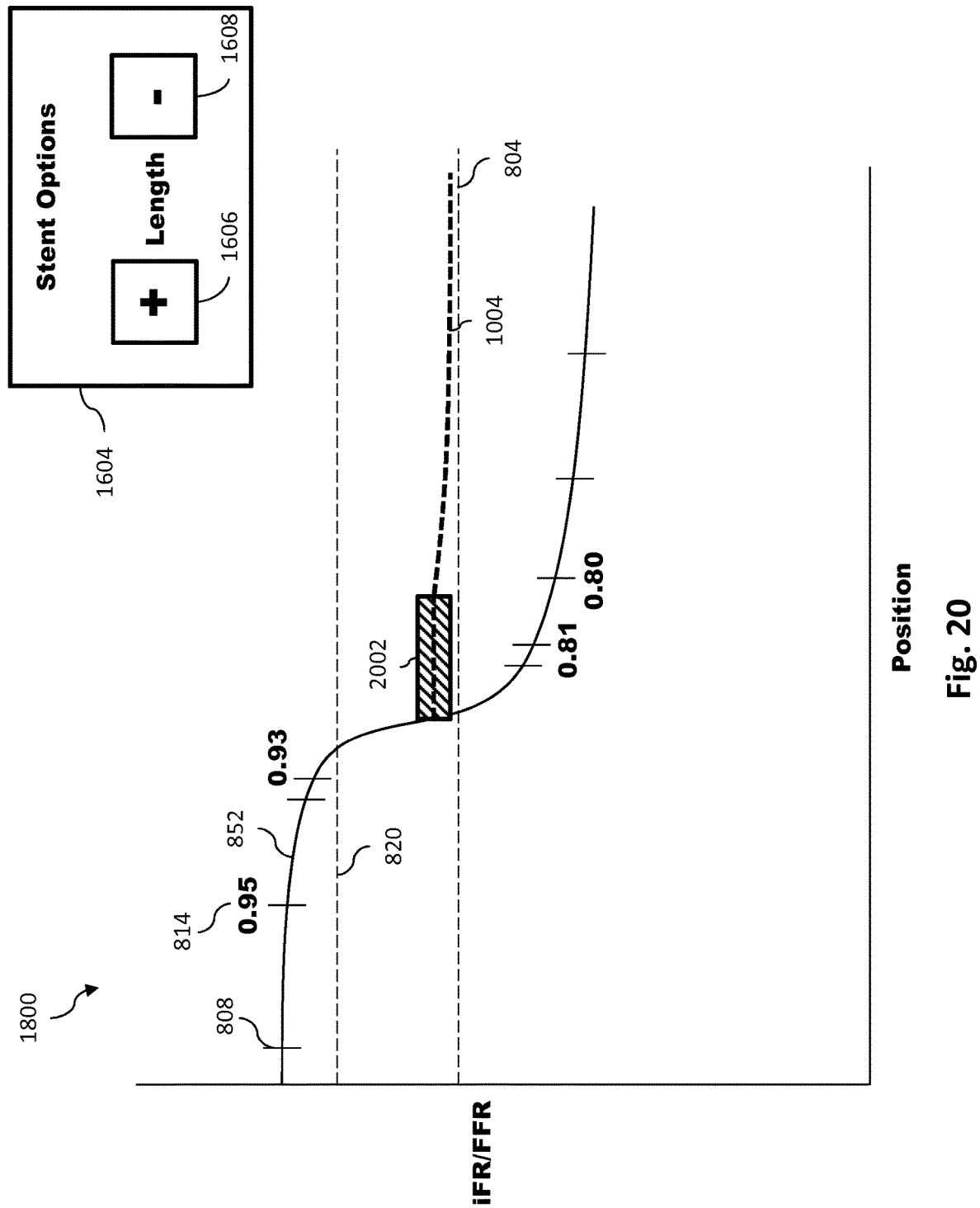
FIG. 20 is a screen display according to another embodiment of the present disclosure.

FIG. 17 illustrates a screen display 1700 (or partial screen display) including a visual representation of a vessel. The data depicted in the screen display 1700 (FIG. 17) corresponds to the data shown in screen display 1800 (FIG. 18). In the embodiment of FIG. 17, the screen display 1700 is shown to be in an intermediate stage in which the length of stent 1702 is being decreased in response to a corresponding user input. In some embodiments, the user input is the selection of the shorten option 1508. Selection of the shorten option 1508 can cause the length of the stent 1702 to be decreased by a fixed or variable amount on one, the other, or both of the ends 1706. In some embodiments, such as when the user input is received on a touch sensitive display, the user input can include a touch on one, the other, or both of the ends 1706 and a drag towards the center of the stent 1702. In the embodiment of FIG. 17, as a result of the user input, the stent 1702 can be shortened by the lengths 1704 on both ends of the stent. While the lengths 1704 on both ends 1706 of the stent 1702 are approximately equal in FIG. 17, it is understood that the stent can be shortened by different lengths on the ends 1706. It is also understood that that the stent 1702 can be shortened on only one end 1706. Screen display 1900 of FIG. 19 shows the stent 1902 with the modified, shorter length in the vessel 702. The data depicted in the screen display 1900 (FIG. 19) corresponds to the data shown in screen display 2000 (FIG. 20).

FIG. 18 illustrates a screen display 1800 (or partial screen display) including a visual representation of a pressure ratio. The data depicted in the screen display 1800 (FIG. 18) corresponds to the data shown in screen display 1700 (FIG. 17). In the embodiment of FIG. 18, the screen display 1800 is shown to be in an intermediate stage in which the length of stent 1802 is being shortened in response to a corresponding user input. In some embodiments, the user input is the selection of the shorten option 1608. Selection of the shorten option 1608 can cause the length of the stent 1802 to be shortened by a fixed amount on one, the other, or both of the ends 1806. In some embodiments, such as when the user input is received on a touch sensitive display, the user input can include a touch on one, the other, or both of the ends 1806 and a drag towards the center of the stent 1802. In the embodiment of FIG. 18, as a result of the user input, the stent 1802 can be shortened by the lengths 1804 on both ends of the stent. In some embodiments, shortening the length of the stent 1802 on the side adjacent the pressure curve 852 can cause the stent 1802 to move from the original position of the stent 1602. That is, shortening the length on the left side of the stent 1602 (in the embodiment of the FIG. 18) results both in the length of the stent changing as well as the position of the stent moving to the right. In some embodiments, shortening the length of the stent 1802 on the side opposite the pressure curve 852 can change the length of the stent without changing the position of the stent. In some embodiments, the corrected pressure ratio curve 1004 can be updated in real time such that as the stent 1802 is being shortened, the curve 1004 is adjusted to reflect the predicted pressure ratio with the stent 1802 having the contemporaneous length. Screen display 2000 of FIG. 20 shows the stent 2002 with the modified, shorter length, as well as the modified position, along the pressure ratio curve 852. The data depicted in the screen display 2000 (FIG. 20) corresponds to the data shown in screen display 1900 (FIG. 19).

Screen display 2000 also provides a corrected pressure ratio curve 1004 that is updated based on the decreased length of the stent 2002. In the embodiment of FIG. 20, the shortened length of the stent 2002 does not provide an improvement to the reduced pressure caused by an obstruction in the vessel 702. Indeed, the curve 1004 of FIG. 20 is farther from the target line 820 than the curve 1004 of FIG. 16 when the stent 1602 had its original length. The curve 1004 of FIG. 20 being farther from the target line 820 is indicative of that fact that that the stent 2002 poorly spans the obstruction in the vessel 702 and is insufficient to remedy the changes in pressure caused by the obstruction. To improve the predicted pressure ratio within the vessel 702 during PCI planning, a clinician can increase the length of the stent, as described below.

Figure 21:
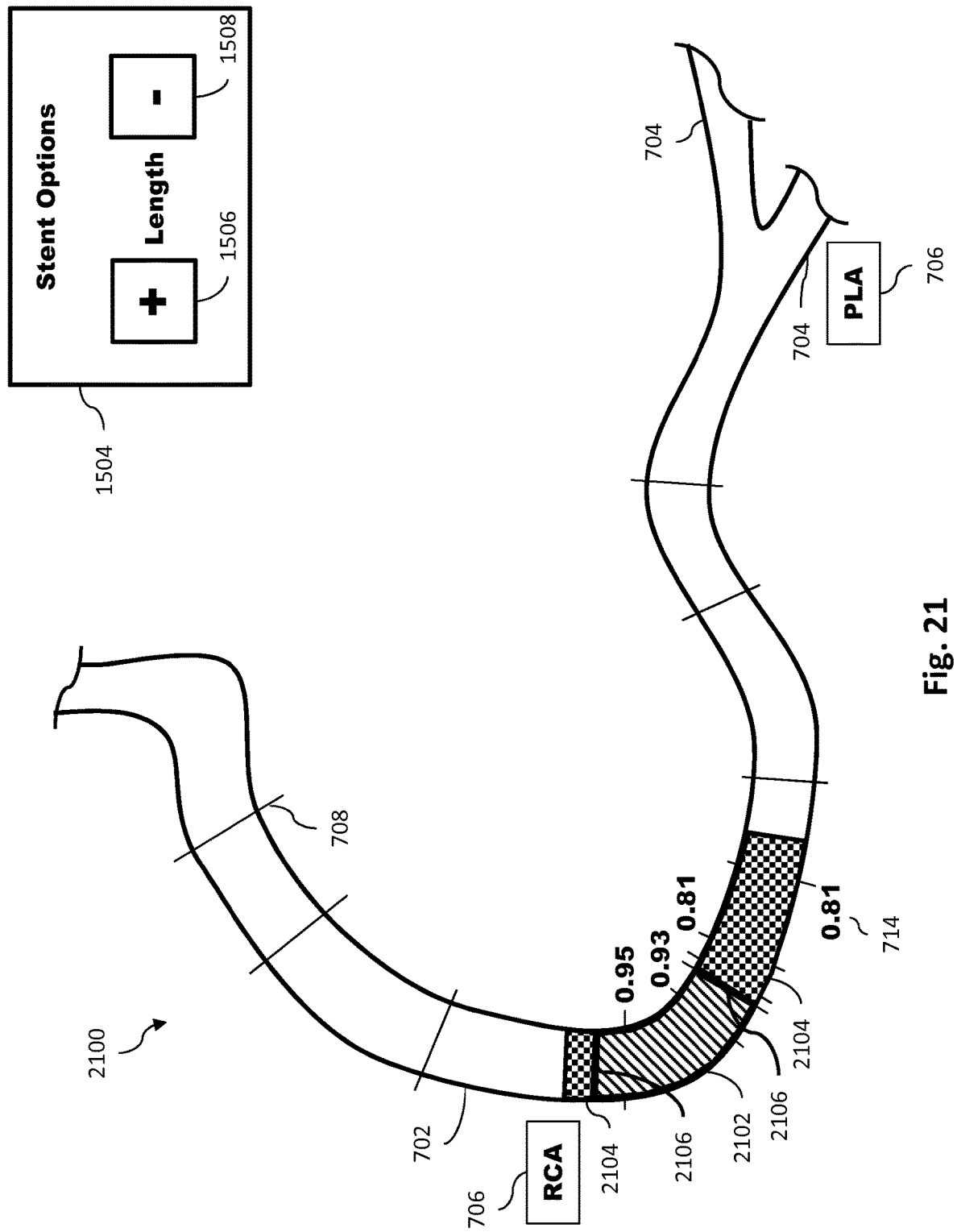
FIG. 21 is a screen display according to another embodiment of the present disclosure.
Figure 22:
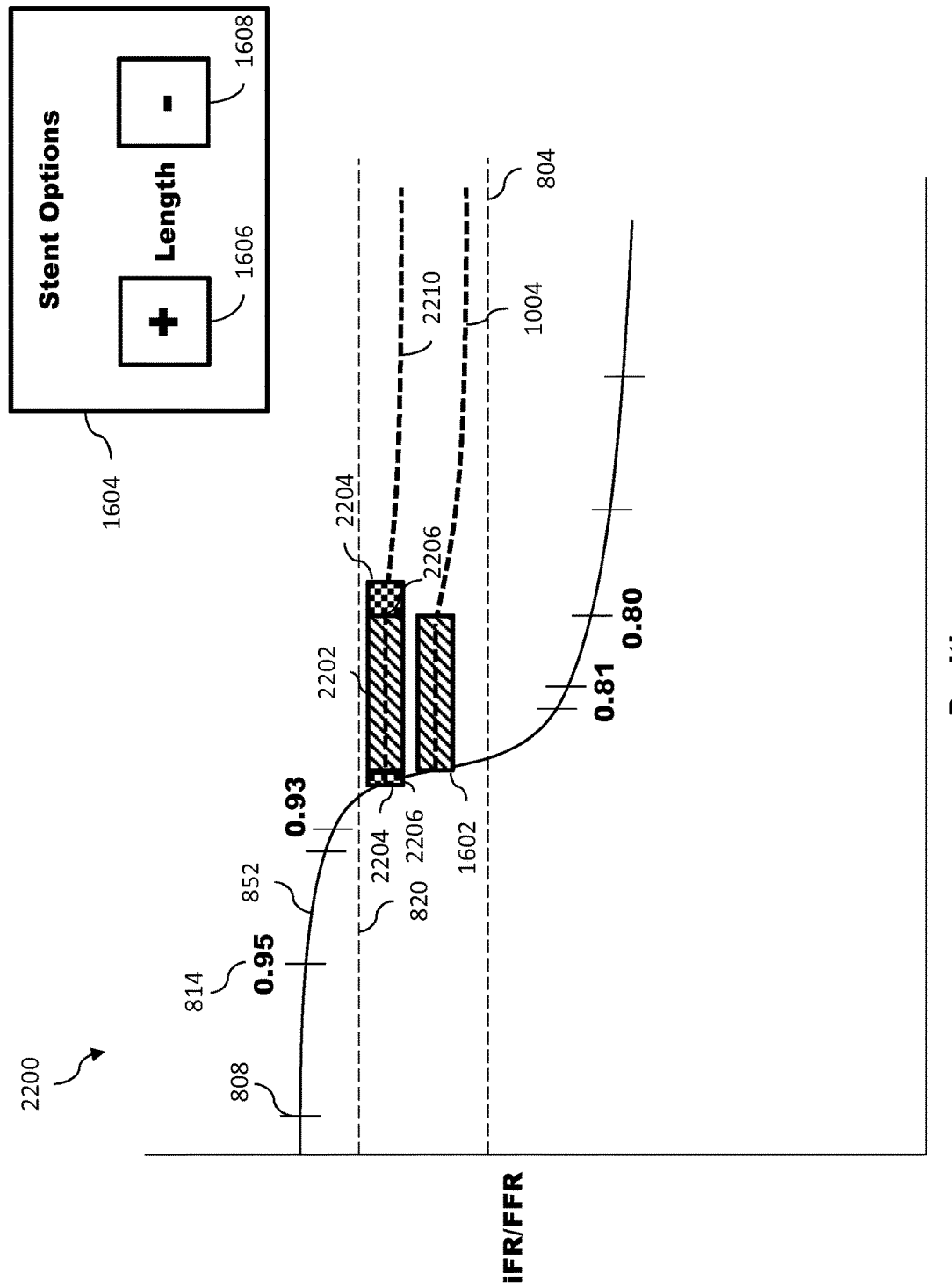
FIG. 22 is a screen display according to another embodiment of the present disclosure.
Figure 23:
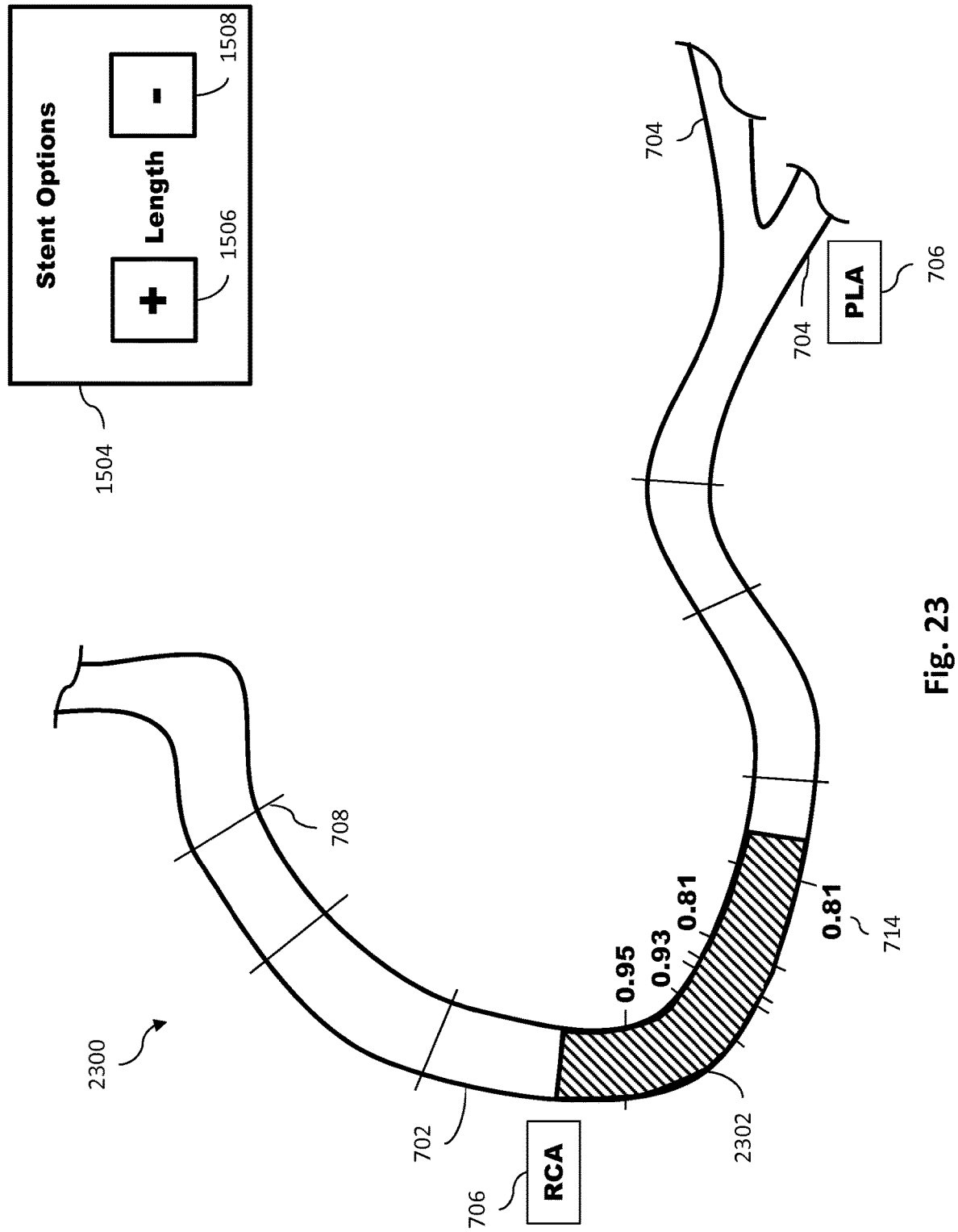
FIG. 23 is a screen display according to another embodiment of the present disclosure.
Figure 24:
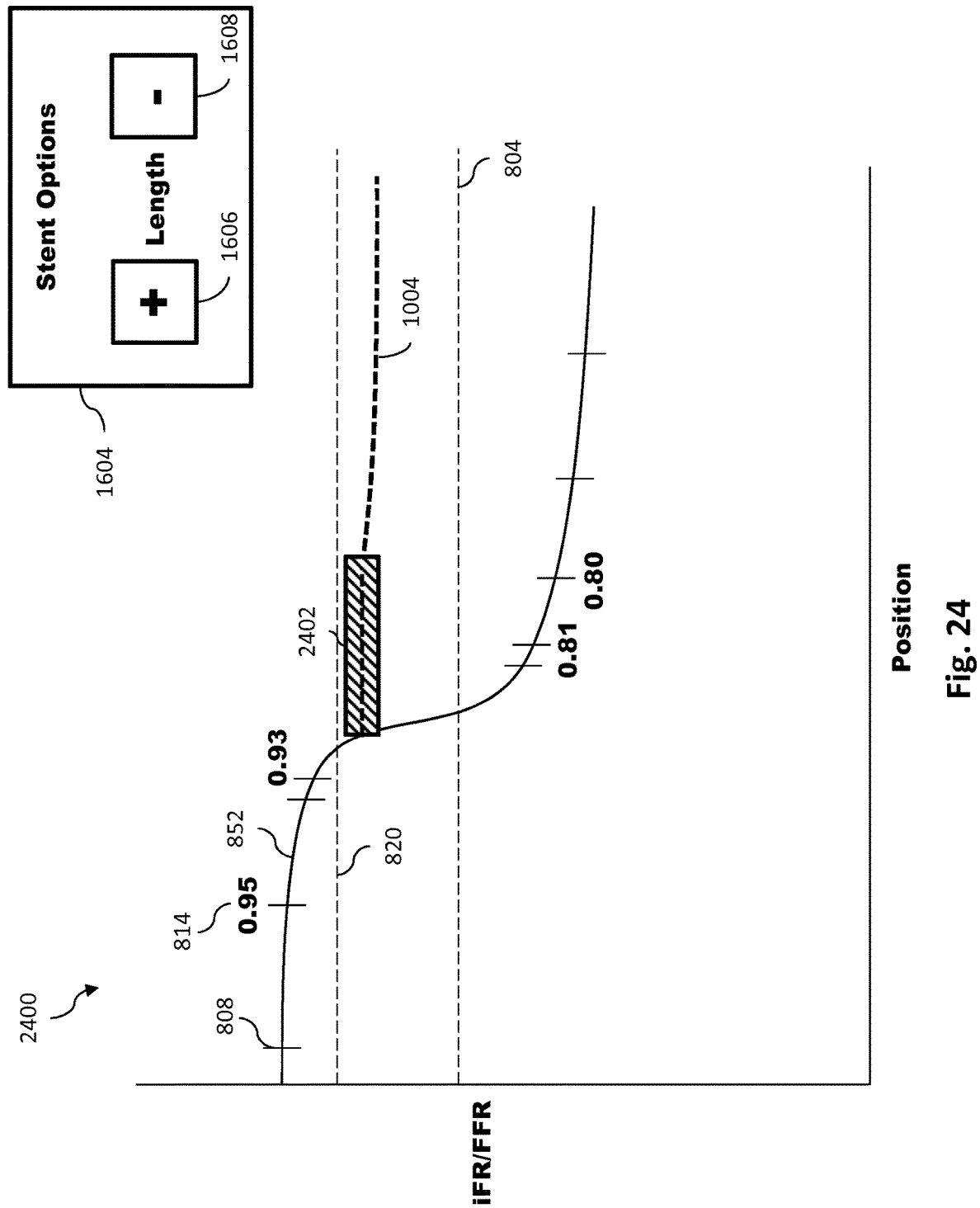
FIG. 24 is a screen display according to another embodiment of the present disclosure.

FIG. 21 illustrates a screen display 2100 (or partial screen display) including a visual representation of a vessel. The data depicted in the screen display 2100 (FIG. 21) corresponds to the data shown in screen display 2200 (FIG. 22). In the embodiment of FIG. 21, the screen display 2100 is shown to be in an intermediate stage in which the length of stent 2102 is being increased in response to a corresponding user input. In some embodiments, the user input is the selection of the lengthen option 1508. Selection of the lengthen option 1508 can cause the length of the stent 1702 to be increased by a fixed or variable amount on one, the other, or both of the ends 2106. In some embodiments, such as when the user input is received on a touch sensitive display, the user input can include a touch on one, the other, or both of the ends 2106 and a drag away from the center of the stent 2102. As a result of the user input, the stent 2106 can be lengthened by the lengths 2104 on both ends 2106 of the stent. As shown in FIG. 21, the end of the stent closer to the change in pressure ratio (e.g., from 0.93 to 0.81) is lengthened such that the stent covers a region of the vessel 702 that is likely to have the obstruction causing the pressure change. While the lengths 2104 on both ends 2106 are different in FIG. 21, it is understood that the lengths 2104 can be the same in other embodiments. It is also understood that that the stent 2106 can be lengthened on only one end 2106. Screen display 2300 of FIG. 23 shows the stent 2302 with the modified, longer length in the vessel 702. The data depicted in the screen display 2300 (FIG. 23) corresponds to the data shown in screen display 2400 (FIG. 24).

FIG. 22 illustrates a screen display 2200 (or partial screen display) including a visual representation of a pressure ratio. The data depicted in the screen display 2200 (FIG. 22) corresponds to the data shown in screen display 2100 (FIG. 21). In the embodiment of FIG. 22, the screen display 220 is shown to be in an intermediate stage in which the length of stent 2202 is being increased in response to a corresponding user input. In some embodiments, the user input is the selection of the lengthen option 1608. Selection of the lengthen option 1608 can cause the length of the stent 2202 to be increased by a fixed or variable amount on one, the other, or both of the ends 2206. In some embodiments, such as when the user input is received on a touch sensitive display, the user input can include a touch on one, the other, or both of the ends 2206 and a drag away from the center of the stent 2202. As a result of the user input, the stent 2202 can be lengthened by the lengths 2204 on both ends 2206 of the stent. In some embodiments, lengthening the stent 2202 adjacent the pressure curve 852 can cause the stent 2202 to move from the original position of the stent 1602. That is, increasing the length on the left side of the stent 1602 (in the embodiment of the FIG. 22) results both in the length of the stent changing as well as the position of the stent moving to the left. In some embodiments, shortening the length of the stent 2202 on the side opposite the pressure curve 852 can change the length of the stent without changing the position of the stent. As shown in FIG. 22, the stent 2202 is lengthened and moved such that the stent covers a region of the curve 852 indicative of a pressure change caused by an obstruction in the vessel. While the lengths 2204 on both ends 2206 are different in FIG. 22, it is understood that the lengths 2204 can be the same in other embodiments. It is also understood that that the stent 2206 can be lengthened on only one end 2206. In some embodiments, the corrected pressure ratio curve 1004 can be updated in real time such that as the stent 2202 is being lengthened, the curve 1004 is adjusted to reflect the predicted pressure ratio with the stent 2202 having the contemporaneous length. Screen display 2400 of FIG. 24 shows the stent 2402 with the modified, longer length, as well as the modified position, along the pressure ratio curve 852. The data depicted in the screen display 2400 (FIG. 24) corresponds to the data shown in screen display 2300 (FIG. 23).

Screen display 2400 also provides a corrected pressure ratio curve 1004 that is updated based on the increased length of the stent 2402. For example, the curve 1004 of FIG. 24 is closer to the target line 820, compared to the curve 1004 of FIG. 16 when the stent 1602 had its original length. The curve 1004 of FIG. 24 being closer to the target line 820 is indicative of that fact that that the stent 2402 is a better length relative to an obstruction in the vessel 702 to remedy the changes in pressure caused by the obstruction. While the curve 1004 is not above the target line 820, a clinician may make a medical determination during PCI planning that the predicted result is the best possible clinical outcome. The virtual/simulated characteristics of the stent 2402 can be correlated to real, physiological parameters of a stent to be positioned within the human vessel to treat a patient based on the PCI planning. Thus, lengthening and shortening the graphical representation of the stent allows a clinician to choose an appropriate physiologic length for the stent being deployed to maximize clinical efficacy during PCI planning.

In some embodiments, changing the length of a stent in the vessel 702 of the screen displays 1700 (FIG. 17) and 2100 (FIG. 21) can cause the stent to be correspondingly shortened or lengthened, respectively, along the pressure ratio curve 852 of the screen displays 1800 (FIG. 12) and 2200 (FIG. 22). Similarly, changing the length of a stent along the pressure ratio curve 852 of the screen displays 1800 (FIG. 12) and 2200 (FIG. 22) can cause the stent to be correspondingly shortened or lengthened, respectively, in the vessel 702 of the screen displays 1700 (FIG. 17) and 2100 (FIG. 21). In this manner, a clinician can conduct PCI planning while interacting directly with a selected one of the screen displays 1700 and 1800, while automatically viewing corresponding changes in the unselected one of the screen displays 1700 and 1800. Likewise, a clinician can conduct PCI planning while interacting directly with a selected one of the screen displays 2100 and 2200, while automatically viewing corresponding changes in the unselected one of the screen displays 2100 and 2200. For example, a clinician can work directly on the screen display 2200 that illustrates the pressure ratio curve 852 and the length of the stent relative to the calculated pressure ratio curve. The stent can be lengthened along the pressure ratio curve 852 such that the corrected pressure ratio curve 1004 more closely matches the ideal pressure ratio line 806 and/or the target line 820. A corresponding change in the length of the stent can be made on the screen display 2100 of the vessel such that a clinician understands the length of the stent to be deployed in the vessel to achieve the corrected pressure ratio curve 852 (FIG. 24).

While the description FIGS. 7-24 describes one modification (e.g., moving the stent, changing the length of the stent), it is understood that multiple operations can be performed on the stent (e.g., one or more instances of moving the stent and one or more instances of changing length of the stent).

Further, while the length and position of a stent have been described in the context of FIGS. 7-24, it is understood that the disclosure similarly applies to other characteristics of the stent, such as diameter and material. For example, physiologic stent sizing can be based on both lesion length and vessel diameter. For example, a 16 mm stent can have diameters in quarter millimeter increments between 2.5 mm and 5.0 mm. In various embodiments, the diameter of the graphical representation of the vessel can be selected to appropriately fit within the visual representation of the vessel or along the pressure curve. A computing device can correlate the diameter of the graphical representation of the stent to a real physiologic diameter of a stent to be inserted into a human vessel. In some embodiments, a clinician can manually input the physiologic stent diameter.

In some embodiments, a computing device can implement QCA (quantitative coronary angiography) to determine the diameter of the vessel in, e.g., an angiographic image. For example, during PCI planning, a clinician can select a position and/or length for a graphical representation of the stent overlaid on the angiographic image of the vessel or a pressure curve. A computing device, using QCA, can determine the real physiologic vessel diameter at both ends of the proposed stent and determine the physiologic stent diameter that is recommended for use within the human vessel. For example, the computing device can select the larger of the two diameters associated with both ends of the proposed stent. A clinician can direct the determination of the physiologic stent diameter or a computing device can automatically determine and provide the physiologic stent diameter.

In some embodiments, intravascular imaging can be used to determine a physiologic stent diameter. For example, a vessel can be imaged using intravascular ultrasound (IVUS), forward looking IVUS (FL-IVUS), optical coherence tomography (OCT), and/or other imaging modalities. In that regard, the methods 500 and 600 can include obtaining intravascular imaging data in some embodiments. The intravascular images can be co-registered with the angiographic data and/or the physiologic data (e.g., pressure measurements, flow measurements, etc.), as described, for example, in U.S. Pat. No. 7,930,014, titled "VASCULAR IMAGE CO-REGISTRATION," which is hereby incorporated by reference in its entirety. For example, during PCI planning, a clinician can select a position and/or length for a graphical representation of the stent overlaid on the angiographic image of the vessel or a pressure curve. A clinician can view the intravascular images at both ends of the proposed stent and determine the physiologic vessel diameters based on the intravascular images. In some embodiments, a computing device can automatically determine the vessel borders and physiologic vessel diameter using intravascular images as described, for example, in U.S. Provisional Application No. 62/024,339, titled "DEVICES, SYSTEMS, AND METHODS FOR IMPROVED ACCURACY MODEL OF VESSEL ANATOMY," and filed Jul. 14, 2014, which is hereby incorporated by reference in its entirety. Based on the determined physiologic vessel diameters, a clinician can determine the physiologic stent diameter or a computing device can automatically determine and provide the physiologic stent diameter. For example, the clinician or computing device can select the larger of the two diameters associated with both ends of the proposed stent.

Figure 25:
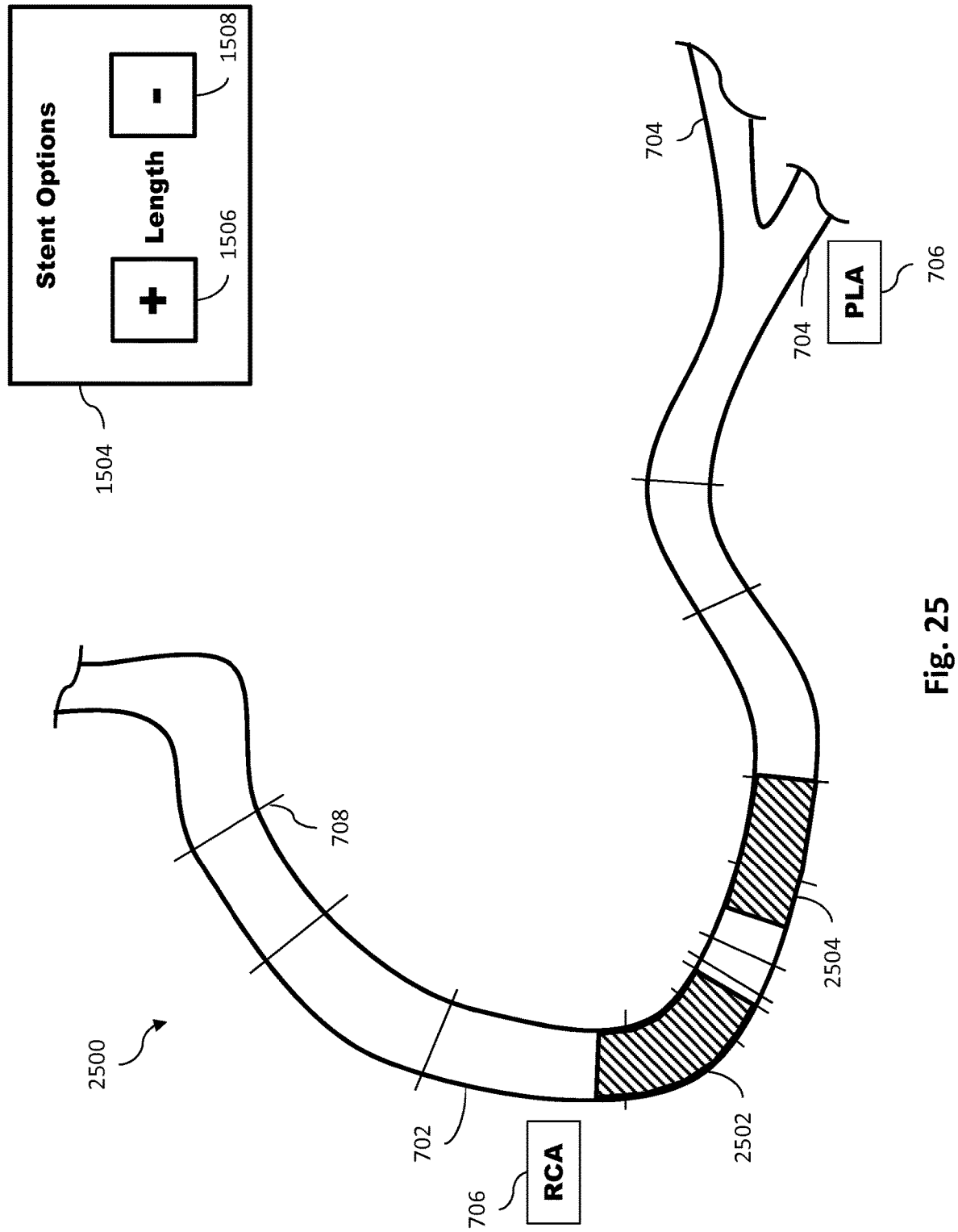
FIG. 25 is a screen display according to another embodiment of the present disclosure.
Figure 26:
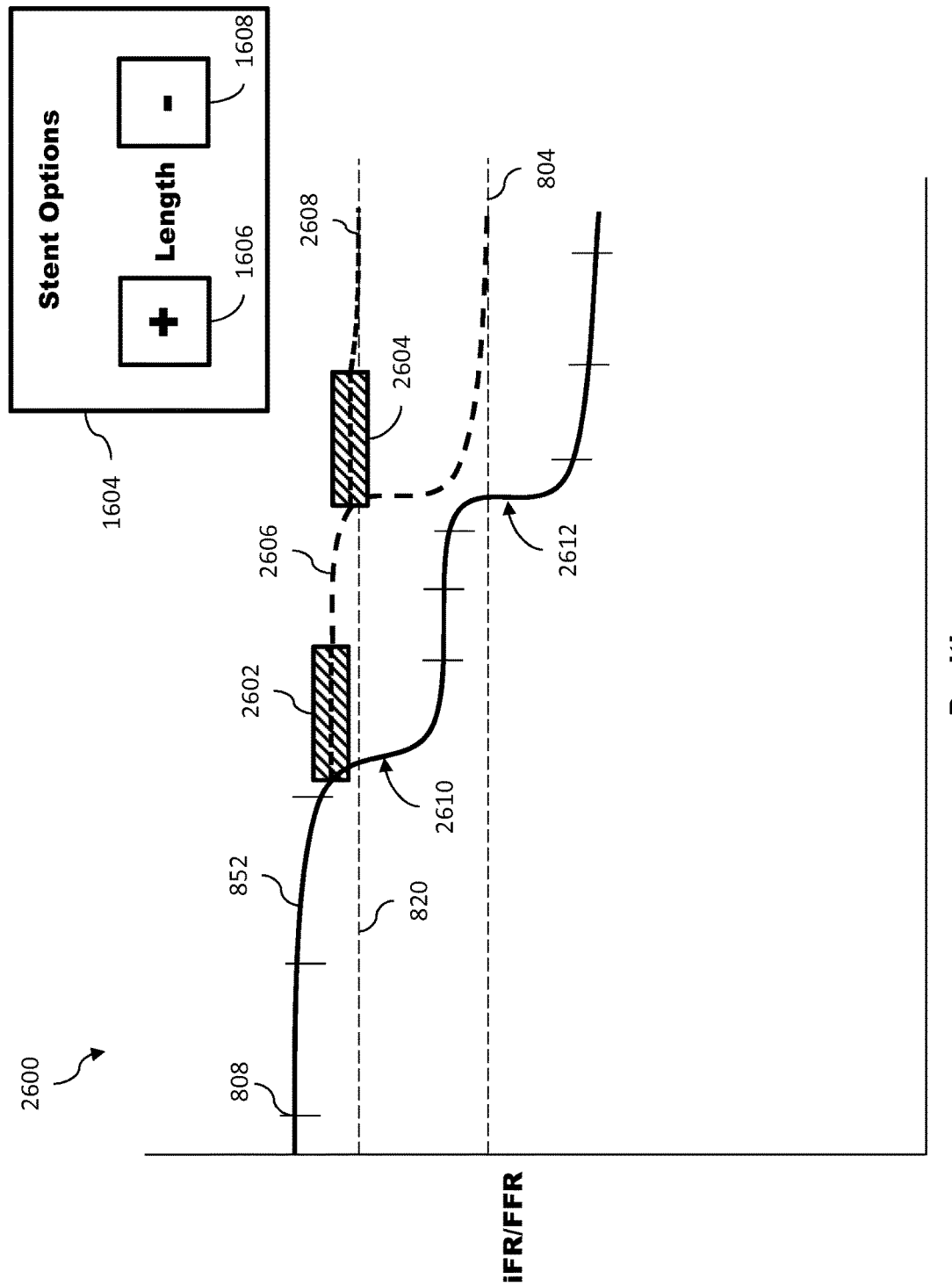
FIG. 26 is a screen display according to another embodiment of the present disclosure.

Further, it is understood that PCI planning can include positioning and individually adjusting more than one stent within the vessel. In that regard, FIGS. 25 and 26 illustrate screen displaying having multiple graphical representations of stents. FIG. 25 illustrates screen display 2500 (or partial screen display) including a visual representation of a vessel having two graphical representations of stents 2502 and 2504. FIG. 26 illustrates a screen display 2600 (or partial screen display) of a visual representation of a pressure ratio having two graphical representations of stents 2602 and 2604. The data depicted in the screen display 2500 (FIG. 25) corresponds to the data shown in screen display 2600 (FIG. 26) and vice versa. PCI planning can include multiple graphical representations of stents when the angiography and/or physiologic data indicate multiple occlusions. For example, the pressure curve 852 of FIG. 26 includes two pressure drops 2610 and 2612 that can be attributable to distinct lesions. PCI planning can include determining to treat one or both of the lesions. While two stents are specifically referred to in the discussion of FIGS. 25 and 26, it is understood that the PCI planning can include any suitable number of stents, including one, two, three, four, five, six, or more.

As shown in FIG. 25, the graphical representations of the stents 2502 and 2504 can each be inserted within the visual representation of the vessel 702. PCI planning can be carried out by moving the graphical representations of the stents 2502 and 2504, changing the lengths/diameters, etc., as described herein. In some embodiments, the characteristics of the graphical representations of the stents 2502 and 2504 can individually modified, such as by first receiving a user input to select a particular stent and then receiving a user input to modify the characteristics of the selected stent. In some embodiments, the characteristics the stents 2502 and 2504 can be inserted and/or modified together, such as a by first receiving a user input to select both stents and receiving a user input to modify the characteristics of both stents.

As shown in FIG. 26, graphical representations of the stents 2602 and 2604 can each be inserted along the visual representation of the pressure ratio. PCI planning can be carried out by moving the graphical representations of the stents 2602 and 2604, changing the lengths/diameters, etc., as described herein. In various embodiments, the characteristics of the graphical representations of the stents 2602 and 2604 can individually or collectively modified. A corrected pressure ratio curve can be associated with each graphical representation of the stent. For example, the corrected pressure ratio curve 2606 is associated with the stent 2602, and the corrected pressure ratio curve 2604 is associated with the stent 2604. A clinician can insert the graphical representation of the stent 2602 along the pressure curve 852. The characteristics of the graphical representation of the stent 2602 can be modified as described herein. The stent 2602 results in some clinical improvement, as indicated by the distal value of corrected pressure ratio curve 2606 being above the threshold 804. The clinician can insert the graphical representation of the stent 2604 along the corrected pressure ratio curve 2606. The characteristics of the graphical representation of the stent 2604 can be modified as described herein. The stent 2604, together with the stent 2602, can result in beneficial clinical outcomes, as indicated by the distal value of the corrected pressure ratio curve 2608 being above the target line 820. The virtual/simulated characteristics of the stents 2602 and 2606 can be correlated to real, physiological parameters of the stents to be positioned within the human vessel to treat a patient based on the PCI planning.

As described herein, modifying the characteristics of one or both of the graphical representations of the stents in in the vessel 702 of the screen displays 2500 (FIG. 25) can cause corresponding the graphical representation of the stent(s) along the pressure curve(s) of the screen display 2600 (FIG. 26) to be similarly modified.

Figure 27:
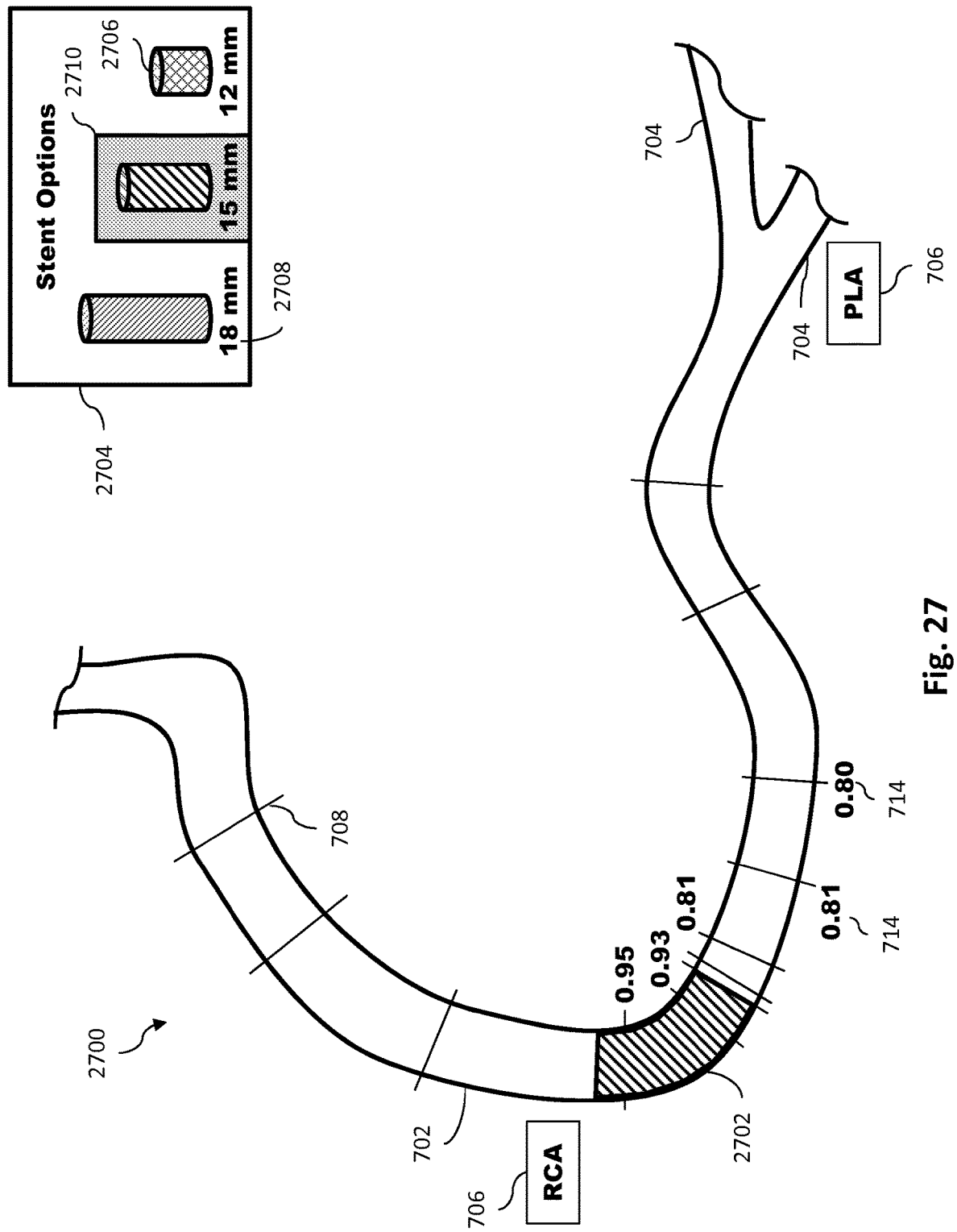
FIG. 27 is a screen display according to another embodiment of the present disclosure.
Figure 28:
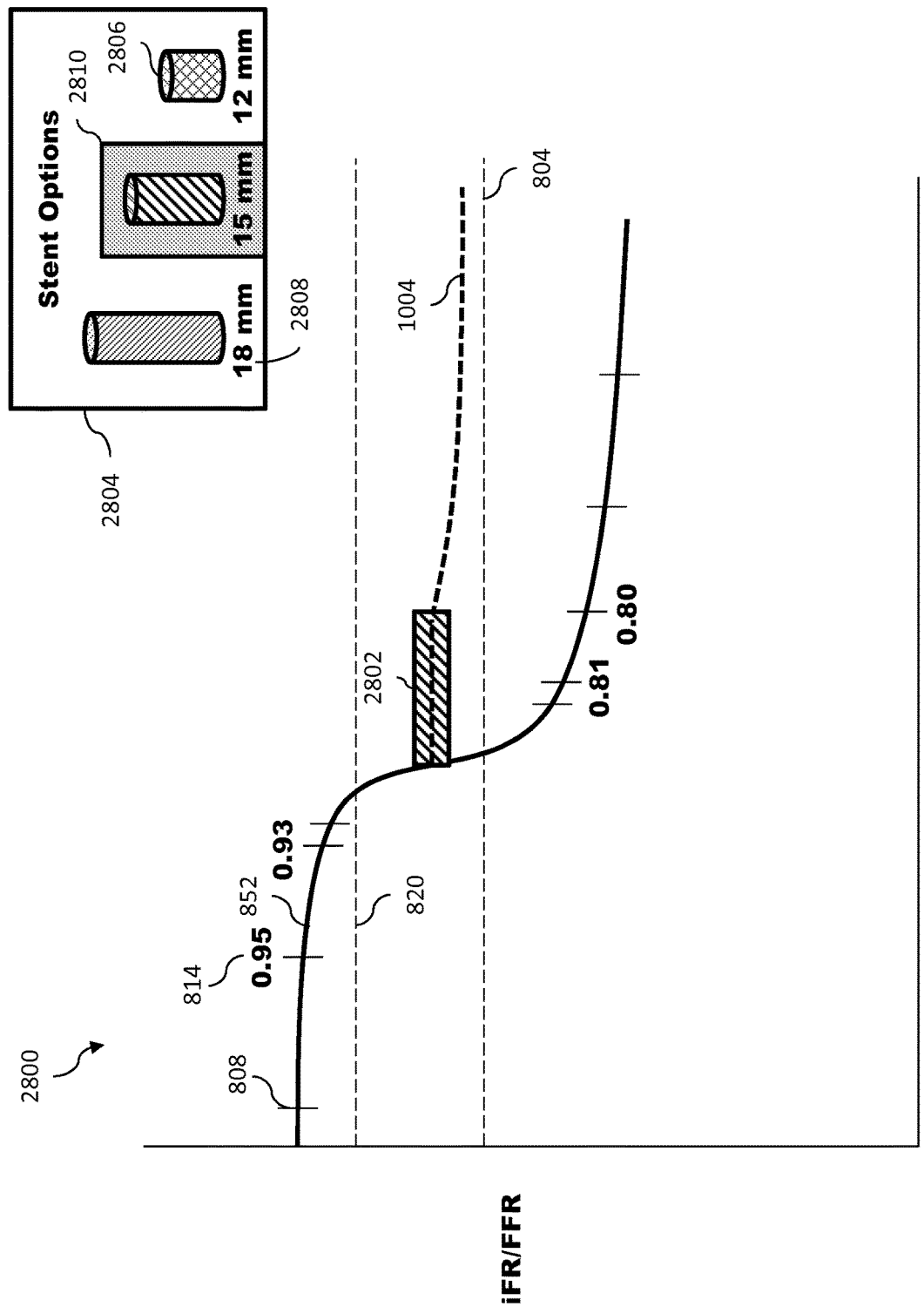
FIG. 28 is a screen display according to another embodiment of the present disclosure.

FIG. 27 illustrates a screen display 2700 (or partial screen display) including a visual representation of a vessel. The data depicted in the screen display 2700 (FIG. 27) corresponds to the data shown in screen display 2800 (FIG. 28). The screen display 2700 includes a stent options menu 2704 including a plurality of stents. While three stents are shown in FIG. 27, it is understood that more or fewer stents can be provided in different embodiments. Each of the plurality of stents can have similar or different physical characteristics, including length, diameter, material, etc. In some embodiments, the stents provided in the menu 2704 correspond to those available to a clinician in a procedure room. For example, a computing device (e.g., computing device 172 of FIG. 4) can access an inventory database of a hospital or other procedure location to determine the types of stents that are in stock and available for a clinician to use. In some embodiments, the stents provided in the menu 2704 corresponded to those available for purchase and use from one or more manufacturers. For example, a computing device can access an inventory database of one or more manufacturers to determine the types of stents that are available for a clinician or hospital to purchase and use. The menu 2704 can include visual representations 2706 of the various stents. Stents of different materials and other properties can be indicated by different colorizations, shading, patterns, etc. A description 2708 can also accompany each of the stents in the menu 2704. For example, the description 2708 can include the length of the stent.

As described above, a user input to insert a stent in the vessel 702 can cause a computing device to automatically determine the recommended physical characteristics of the stent. In some instances, the recommended physical characteristics may not correspond to an stent that is in stock and available for a clinician to use. For example, a recommended physiologic length determined by the computing device may be 15.5 mm, while actual stents are only available in increments of 1 mm. Further, the stent can be identified by both the physiologic length and the physiologic diameter. In such embodiments a computing device can automatically determine which stent among the available stents most closely matches the recommended physical characteristics and provide the most closely matching stent in the vessel 702. For example, a computing device may provide a 16 mm long and 3.0 mm diameter stent that is in stock and available for a clinician in the vessel 702, when 15.5 mm is the recommended stent length. The physiologic stent diameter can be determined as described herein. In some embodiments, the clinician can determine and provide the length and/or diameter for the stent to a computing device. The computing device can access the inventory database and recommend suitable stent(s) based on the inputted length and/or diameter. A user can change the recommended stent by selecting another option from the menu 2704. A user can also modify the characteristics of the stent, such as location, diameter, and length, as described above. In some embodiments, the menu 2704 provides only stents that are in stock and available, while in other embodiments, menu 2704 provides all stents at a hospital, regardless of whether they are in stock or available. An indicator, such as a symbol or coloring, can be disposed adjacent to either those that are available or those that are unavailable to visually distinguish them from the others. In other embodiments, the computing device does not automatically select from among the plurality of stents. Rather, a clinician is able to individually select from the menu 2704 to determine which stent is most suitable. The visual representation of the automatically recommended or clinician selected stent 2702 that is inserted in the vessel 702 can be indicated by highlighting 2710 in the menu 2704. The stent 2702 can be modified as described in the context of FIGS. 7-24.

FIG. 28 illustrates a screen display 2800 (or partial screen display) including a visual representation of a pressure ratio. The data depicted in the screen display 2800 (FIG. 28) corresponds to the data shown in screen display 2700 (FIG. 27). The screen display 2800 includes a stent options menu 2804 including a plurality of stents. While three stents are shown in FIG. 28, it is understood that more or fewer stents can be provided in different embodiments. In some embodiments, the stents provided in the menu 2804 correspond to those available to a clinician in a procedure room. For example, a computing device (e.g., computing device 172 of FIG. 4) can access an inventory database of a hospital or other procedure location to determine the types of stents that are in stock and available for a clinician to use. In some embodiments, the stents provided in the menu 2804 corresponded to those available for purchase and use from one or more manufacturers. For example, a computing device can access an inventory database of one or more manufacturers to determine the types of stents that are available for a clinician or hospital to purchase and use. The menu 2804 can include visual representations 2806 of the various stents. Stents of different materials and other properties can be indicated by different colorizations, shading, patterns, etc. A description 2808 can also accompany each of the stents in the menu 2804. For example, the description 2808 can include the stent length.

As described above, a user input to insert a stent along the pressure ratio curve 852 can cause a computing device to automatically determine the recommended physical characteristics of the stent. In some instances, the recommended physical characteristics may not correspond to a stent that is in stock and available for a clinician to use. For example, a recommend physical length determined by the computing device may be 15.5 mm, while stents are only available in increments of 1 mm. Further, the stent can be identified by both the physiologic length and the physiologic diameter. In some embodiments, the clinician can determine and provide the length and/or diameter for the stent to a computing device. The computing device can access the inventory database and recommend suitable stent(s) based on the inputted length and/or diameter. In such embodiments, a computing device can automatically determine which stent among the available stents most closely matches the recommended physical characteristics and provided the most closely matching stent along the curve 852. For example, a computing device may provide a 16 mm long and 3.0 mm diameter stent that is in stock and available for a clinician along the curve 852, when 15.5 mm is the recommended stent length. The physiologic stent diameter can be determined as described herein. A user can change the recommended stent by selecting another option from the menu 2804. A user can also modify the characteristics of the stent, such as location, diameter, and length, as described above. In some embodiments, the menu 2804 provides only stents that are in stock and available, while in other embodiments, menu 2804 provides all stents at a hospital, regardless of whether they are in stock or available. An indicator, such as a symbol or coloring, can be disposed adjacent to either those that are available or those that are unavailable to visually distinguish them from the others. In other embodiments, the computing device does not automatically select from among the plurality of stents. Rather, a clinician is able to individually select from the menu 2804 to determine which stent is most suitable. The graphical representation of the automatically recommended or clinician selected stent that is inserted along the curve 852 can be indicated by highlighting 2510 in the menu 2804. The stent 2802 can be modified as described in the context of FIGS. 7-24.

In some embodiments, inserting a stent from the menu 2704 in the vessel 702 of the screen display 2700 (FIG. 27) can cause the stent to be correspondingly inserted along the pressure ratio curve 852 of the screen display 2800 (FIG. 28). Similarly, inserting a stent from the menu 2804 along the pressure ratio curve 852 of the screen display 2800 (FIG. 28) can cause the stent to be correspondingly inserted in the vessel 702 of the screen display 2700 (FIG. 27). In this manner, a clinician can conduct PCI planning while interacting directly with a selected one of the screen displays 2700 and 2800, while automatically viewing corresponding changes in the unselected one of the screen displays 2700 and 2800. For example, a clinician can work directly on the screen display 2800 that illustrates the pressure ratio curve 852 and the position/length the stent relative to the calculated pressure ratio curve. A stent from among the plurality of available stents can be selected and inserted along the pressure ratio curve 852 such that the corrected pressure ratio curve 1004 more closely matches the ideal pressure ratio line 806 and/or the target line 820. A corresponding stent can be inserted in the vessel 702 of the screen display 2700 of the vessel such that a clinician understands which of the available stents should be deployed in the vessel to achieve the corrected pressure ratio curve 1004. In the embodiment of FIG. 2800, a longer stent is necessary to bring the corrected pressure ratio curve 1004 closer to the threshold 804.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for evaluating a vessel of a patient, comprising:
 a first instrument sized and shaped for introduction into the vessel of the patient; and
 a processing system communicatively coupled to the first instrument, a second instrument, and a display device, the processing system configured to:
  receive pressure measurements from the first and second instruments while the first instrument is moved longitudinally through the vessel and the second instrument remains stationary within the vessel;
  output, to the display device, a screen display including:
   a visualization based on pressure measurements received from the first instrument and the second instrument; and
   a visual representation of a vessel;
  receive a user input to modify the visualization to simulate a therapeutic procedure; and
  update the screen display, in response to the user input, including modifying the visualization based on the user input.

2. The system of claim 1, wherein the visual representation of the vessel includes an angiographic image of the vessel, and wherein the visualization includes a graphical overlay on the angiographic image.

3. The system of claim 1, wherein the visualization includes a graphical representation of a stent positioned in the visual representation of the vessel, and wherein the therapeutic procedure is a percutaneous coronary intervention.

4. The system of claim 3, wherein the processing system is further configured to:
 determine physiological parameters for a stent to be deployed in the vessel based on the characteristics of the graphical representation of the stent.

5. The system of claim 3, wherein:
 the physiological parameters include at least one of stent position, stent length, and stent diameter; and the characteristics of the graphical representation of the stent include at least one of: position, length, and diameter.

6. The system of claim 5, wherein the processing system is further configured to automatically calculate at least one of the stent length and the length of the graphical representation of the stent based on at least one of the angiography data, the received pressure measurements, and a pressure ratio calculated based on the received pressure measurements, wherein the visualization includes a graphical representation of a stent having the calculated length.

7. The system of claim 5, wherein the processing system is further configured to determine at least one of the stent length and the length of the graphical representation of the stent based on the user input, wherein the visualization includes a graphical representation of a stent having the determined length.

8. The system of claim 5, wherein the processing system is further configured to automatically calculate at least one of the stent diameter and the diameter of the graphical representation of the stent based on at least one of angiography data and intravascular ultrasound (IVUS) data.

9. The system of claim 5, wherein the processing system is configured receive a user input by receiving a user input to move the graphical representation of the stent within the visual representation of the vessel, and wherein the processing system is configured to modify the visualization by outputting the graphical representation of the stent at a location based on the user input.

10. The system of claim 5, wherein the processing system is configured receive a user input by receiving a user input to change a length of the graphical representation of the stent within the vessel, and wherein the processing system is configured to modify the visualization by outputting the graphical representation of the stent with the length based on the received user input.

11. The system of claim 5, wherein the processing system is further configured to output a plurality of graphical representations of stents.

12. The system of claim 11, wherein the processing system is further configured to compile the plurality of graphical representations of stents based on an inventory database of stents associated with a clinical environment.

13. The system of claim 11, wherein the processing system is further configured to do at least one of:
receive a user input to select one of the plurality of graphical representations of stents, wherein the visualization includes the selected graphical representation of a stent from among the plurality of graphical representations of stents; and
automatically select a graphical representation of a stent from among a plurality of graphical representations of stents based on at least one of the angiography data, the received pressure measurements, and a pressure ratio calculated based on the received pressure measurements, wherein the visualization includes the automatically selected graphical representation of a stent from among the plurality of graphical representations of stents.

14. The system of claim 5, wherein the processing system is further configured to calculate a pressure ratio within the vessel based on the receive pressure measurements, and wherein the visualization further includes the calculated pressure ratio.

15. The system of claim 14, wherein the visualization further includes at least one of:
a marker indicative of a location within the vessel associated with the obtained pressure measurements;
the calculated pressure ratio positioned adjacent to the marker indicative of the location within the vessel.

16. The system of claim 15, wherein successive markers are positioned along the visual representation of the vessel at unequally spaced intervals.

17. The system of claim 5, wherein the processing system is further configured to automatically identify the vessel, and wherein the visualization further includes a label indicative of the determined identity of the vessel.

18. A method of evaluating a vessel of a patient, comprising:
outputting, to a display device, a screen display including:
a visualization based on pressure measurements obtained from a first instrument and a second instrument while the first instrument is moved longitudinally through the vessel and the second instrument remains stationary within the vessel; and
a visual representation of a vessel;
receiving a user input to modify the visualization to simulate a therapeutic procedure; and
updating the screen display, in response to the user input, including modifying the visualization based on the user input.

19. The method of claim 18, further comprising obtaining angiography data simultaneously as obtaining the pressure measurements, wherein the visual representation of the vessel includes an angiographic image of the vessel, and wherein the visualization includes a graphical overlay on the angiographic image.

20. The method of claim 19, wherein the visualization includes a graphical representation of a stent positioned in the visual representation of the vessel, and wherein the therapeutic procedure is a percutaneous coronary intervention.

* * * * *